US012698292B2

(12) United States Patent
Li et al.

(10) Patent No.: US 12,698,292 B2
(45) Date of Patent: Aug. 4, 2026

(54) TOXIN MOLECULE SUITABLE FOR ANTIBODY-DRUG CONJUGATE

(71) Applicants: MINGHUI PHARMACEUTICAL (HANGZHOU) LIMITED, Hangzhou (CN); MINGHUI PHARMACEUTICAL (SHANGHAI) LIMITED, Shanghai (CN)

(72) Inventors: Ao Li, Shanghai (CN); Yile Chen, Hangzhou (CN); Guoqing Cao, Hangzhou (CN)

(73) Assignees: MINGHUI PHARMACEUTICAL (HANGZHOU) LIMITED, Hangzhou (CN); MINGHUI PHARMACEUTICAL (SHANGHAI) LIMITED, Shanghai (CN)

( * ) Notice: Subject to any disclaimer, the term of this patent is extended or adjusted under 35 U.S.C. 154(b) by 403 days.

(21) Appl. No.: 18/274,905

(22) PCT Filed: Jan. 28, 2022

(86) PCT No.: PCT/CN2022/074825
§ 371 (c)(1),
(2) Date: Jul. 28, 2023

(87) PCT Pub. No.: WO2022/161479
PCT Pub. Date: Aug. 4, 2022

(65) Prior Publication Data

US 2024/0132515 A1 Apr. 25, 2024

(30) Foreign Application Priority Data

Jan. 29, 2021 (CN) ......................... 202110127049.3

(51) Int. Cl.
*C07D 491/22* (2006.01)
*A61P 35/00* (2006.01)

(52) U.S. Cl.
CPC ............ *C07D 491/22* (2013.01); *A61P 35/00* (2018.01)

(58) Field of Classification Search
CPC .................................................... C07D 491/22
See application file for complete search history.

(56) References Cited

U.S. PATENT DOCUMENTS

| | | | |
|---|---|---|---|
| 6,407,115 | B1 | 6/2002 | Terasawa et al. |
| 9,808,537 | B2 | 11/2017 | Masuda et al. |
| 10,906,974 | B2 | 2/2021 | Iida et al. |
| 2022/0233708 | A1 | 7/2022 | Bao et al. |

FOREIGN PATENT DOCUMENTS

| | | | |
|---|---|---|---|
| CN | 104755494 | A | 7/2015 |
| CN | 109106951 | A | 1/2019 |
| CN | 110382535 | A | 10/2019 |
| WO | 2020259258 | A1 | 12/2020 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "Zinc—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Kawakami, Suppression of pancreatic fistula using drugs—Verification using a rat pancreatic fistula model, Abstracts of the Annual Congress of Japan Surgical Society, 117:2037 (2017).*
English translation International Search Report mailed Mar. 30, 2022 corresponding to PCT/CN2022/074825, 6 pages.

* cited by examiner

*Primary Examiner* — Nizal S Chandrakumar
(74) *Attorney, Agent, or Firm* — ICE MILLER LLP

(57) ABSTRACT

The present invention provides a toxin molecule suitable for an antibody drug conjugate. In particular, the present invention provides a compound represented by formula (I) below or a pharmaceutically acceptable salt or hydrate thereof. The compound of the present invention can be used in the preparation of a pharmaceutical composition for treating diseases associated with tumor cell proliferation.

I

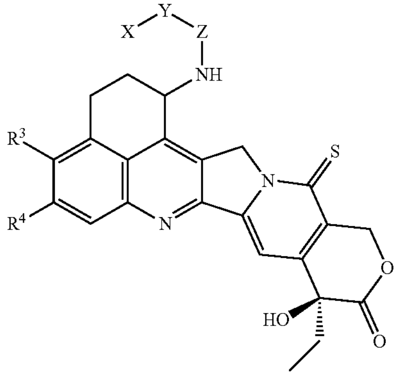

3 Claims, No Drawings

TOXIN MOLECULE SUITABLE FOR ANTIBODY-DRUG CONJUGATE

TECHNICAL FIELD

The invention relates to the field of pharmaceutical chemistry, in particular, the present invention provides a toxin molecule with tumor cell proliferation inhibitory activity.

BACKGROUND

Antibody drug conjugate (ADC) connects monoclonal antibodies or antibody fragments to biologically active cytotoxins through stable chemical conjugate compound, which fully utilizes the specificity of antibodies binding to antigens on the surface of normal and tumor cell surface, and the efficiency of cytotoxins, while avoiding defects such as low efficacy of the former, and excessive toxic side effects of the latter. This also means that, compared to previous traditional chemotherapy drugs, antibody-drug conjugates can more accurately bind to tumor cells and have less impact on normal cells.

At present, many ADC drugs have been used in clinical or clinical research, such as Kadcyla, which is an ADC drug formed by Trastuzumab targeting Her2, and DM1. At the same time, patents for antibodies and ADC drugs targeting B7H3 have been reported.

There are several types of cytotoxic small molecules used for antibody drug conjugates; one of them is camptothecin derivatives, which have anti-tumor effects by inhibiting topoisomerase I. The application of camptothecin derivative exatecan in antibody drug conjugate (ADC) has been reported, but there is still need for developing more effective ADC drugs in the field.

DNA topoisomerase (Topo) is a widespread essential enzyme in organisms, which is involved in all key intranuclear processes such as DNA replication, transcription, recombination, and repairment. According to the difference between instant DNA strand breaks caused by topoisomerase, topoisomerase can be divided into two categories: topoisomerase I and topoisomerase II. Topoisomerase I and topoisomerase II together catalyze the unwinding of superhelical DNA during DNA replication, but topoisomerase II is involved in double-stranded breaks, while topoisomerase I only causes single-stranded breaks. Camptothecin and its analogs terminate progressive unwinding by reversibly binding to the DNA topoisomerase I-DNA complex, forming a ternary complex of camptothecin and its analogs-DNA topoisomerase I-DNA, which ultimately makes the replication forks crash into the ternary complex and induces unrepairable DNA breaks, thereby causing cell death.

SUMMARY OF THE INVENTION

The purpose of the present invention is to provide a toxin molecule suitable for antibody conjugated drugs.

The first aspect of the present invention provides a compound as shown in formula (I), or a pharmaceutically acceptable salt, or a hydrate thereof:

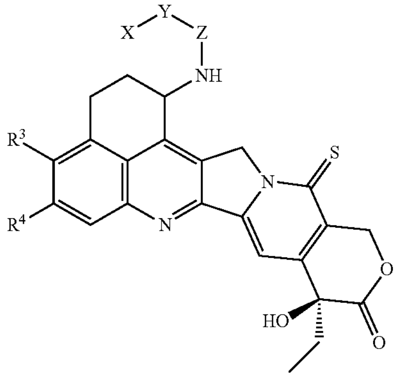

I

X is selected from the group consisting of H, OH, $NH_2$, and $NHR^0$;

Y is selected from the group consisting of $(CR^1R^2)_n$;

Z is selected from the group consisting of chemical bond, C(O), C(S), C(NH), $S(O)_2$, and S(O);

$R^0$ is selected from the group consisting of $C_1$-$C_8$ alkyl, $C_1$-$C_8$ haloalkyl, $C_1$-$C_8$ deuterated alkyl, $C_1$-$C_8$ alkoxy, $C_1$-$C_8$ hydroxyalkyl, $C_3$-$C_8$ cycloalkyl, and 3-12 membered heterocyclyl;

$R^1$ and $R^2$ are independently selected from the group consisting of hydrogen, deuterium, halogen, $C_1$-$C_8$ alkyl, $C_1$-$C_8$ haloalkyl, $C_1$-$C_8$ deuterated alkyl, $C_1$-$C_8$ alkoxy, hydroxyl, amino, cyano, nitro, $C_1$-$C_8$ hydroxyalkyl, $C_3$-$C_8$ cycloalkyl and 3-12 membered heterocyclyl;

or, $R^1$ and $R^2$ together with their attached carbon atoms form a $C_3$-$C_8$ cycloalkyl or 3-12 membered heterocyclyl;

$R^3$ and $R^4$ are independently selected from the group consisting of hydrogen, deuterium, halogen, $C_1$-$C_8$ alkyl, $C_1$-$C_8$ haloalkyl, and $C_1$-$C_8$ deuterated alkyl;

or, $R^3$ and $R^4$ together with their attached carbon atoms form a structure selected from the following group: saturated or unsaturated 5-12 membered carbocyclic ring, saturated or unsaturated 5-12 membered heterocycle;

n is selected from 0, 1, 2, or 3 (preferably 0, 1, or 2);

and, when n is 2 or 3, each $CR^1R^2$ can be the same or different.

unless otherwise specified, the groups of the invention can be substituted by substituents selected from the group consisting of halogen, cyano, nitro, hydroxyl, amino, $C_1$-$C_6$ alkyl-amino, $C_1$-$C_6$ alkyl, $C_2$-$C_6$ alkenyl, $C_2$-$C_6$ alkynyl, $C_1$-$C_6$ alkoxy, halogenated $C_1$-$C_6$ alkyl, halogenated $C_2$-$C_6$ alkenyl, halogenated $C_2$-$C_6$ alkynyl, halogenated $C_1$-$C_6$ alkoxy, allyl, benzyl, $C_6$-$C_{12}$ aryl, $C_1$-$C_6$ alkoxy-$C_1$-$C_6$ alkyl, $C_1$-$C_6$ alkoxy-carbonyl, phenoxy carbonyl, $C_2$-$C_6$ alkynyl-carbonyl, $C_2$-$C_6$ alkenyl-carbonyl, $C_3$-$C_6$ cycloalkyl-carbonyl, $C_1$-$C_6$ alkyl sulfonyl.

In another preferred embodiment, $R^3$ is selected from the group consisting of $C_1$-$C_8$ alkyl, $C_1$-$C_8$ haloalkyl, and $C_1$-$C_8$ deuterated alkyl.

In another preferred embodiment, $R^4$ is selected from the group consisting of hydrogen, deuterium, and halogen.

In another preferred embodiment, the compound has a structure as shown in the following formula:

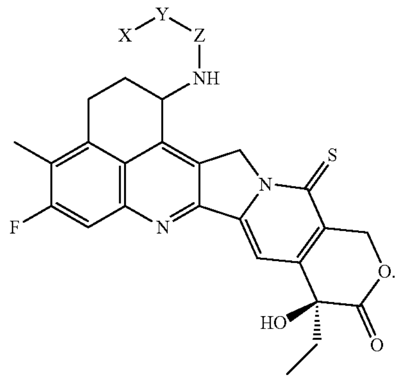

In another preferred embodiment, Z is chemical bond, or C(O).

In another preferred embodiment, X is H, OH, or $NH_2$.

In another preferred embodiment, Y is selected from the group consisting of $(CR^1R^2)_n$;

wherein, $R^1$ and $R^2$ are independently selected from the group consisting of hydrogen, deuterium, halogen, $C_1$-$C_8$ alkyl, $C_1$-$C_8$ haloalkyl, $C_1$-$C_8$ deuterated alkyl, $C_1$-$C_8$ hydroxyalkyl, $C_3$-$C_6$ cycloalkyl, or 3-6 membered heterocyclyl; or, $R^1$ and $R^2$ together with their attached carbon atoms form a $C_3$-$C_6$ cycloalkyl or 3-6 membered heterocyclyl; and $C_1$-$C_8$ alkyl can be optionally substituted by substituents selected from the group consisting of $C_6$-$C_{10}$ aryl, 5-10 membered heteroaryl, $C_3$-$C_6$ cycloalkyl, and 3-6 membered heterocyclyl.

n is selected from 0, 1, 2, or 3;

and when n is 2 or 3, each $CR^1R^2$ can be the same or different.

In another preferred embodiment, the compound has a structure as shown in the following formula:

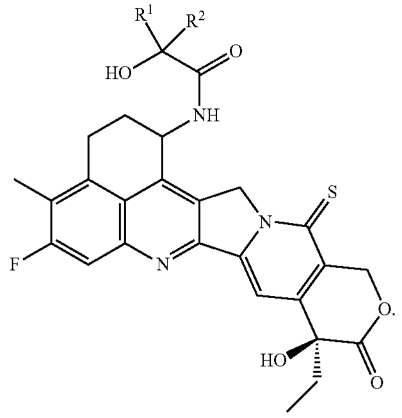

In another preferred embodiment, the compound has a structure as shown in the following formula:

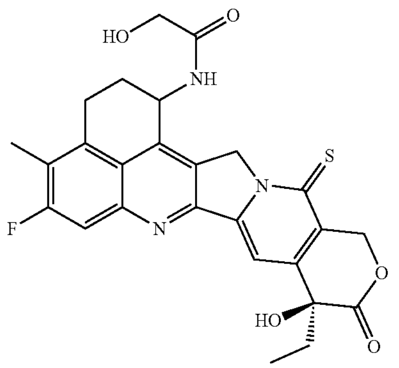

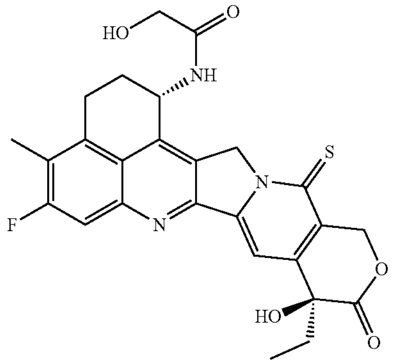

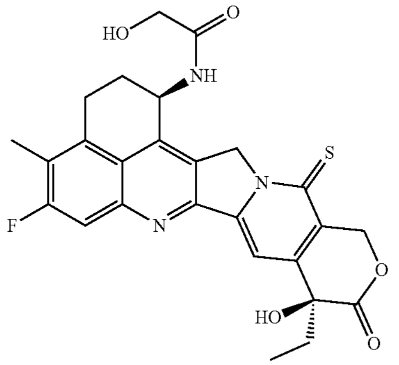

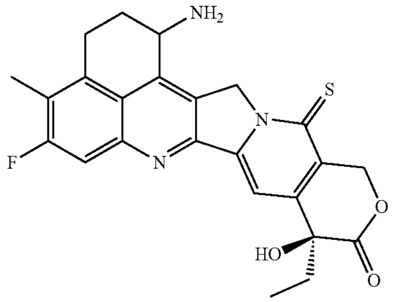

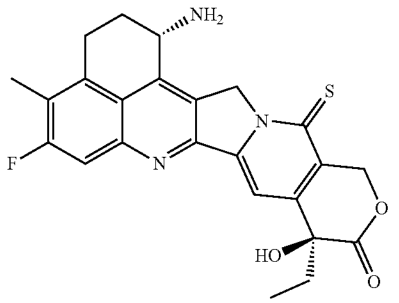

-continued
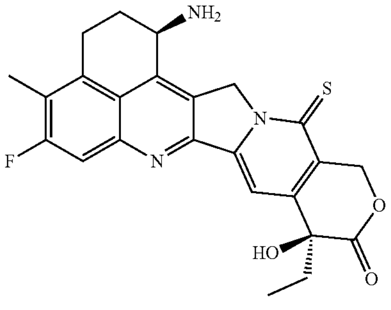
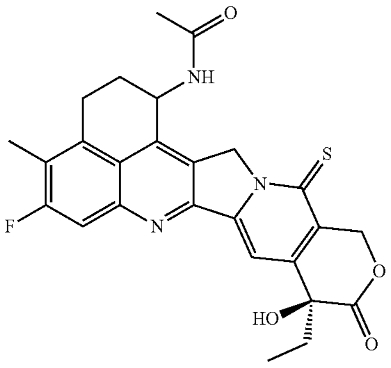
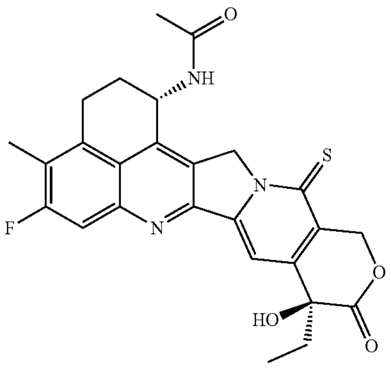
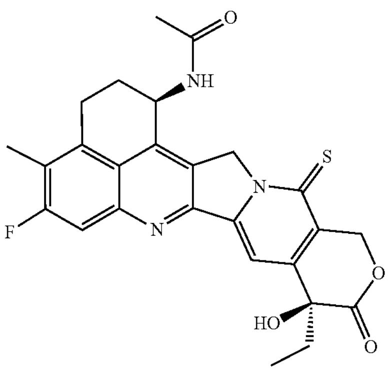
-continued
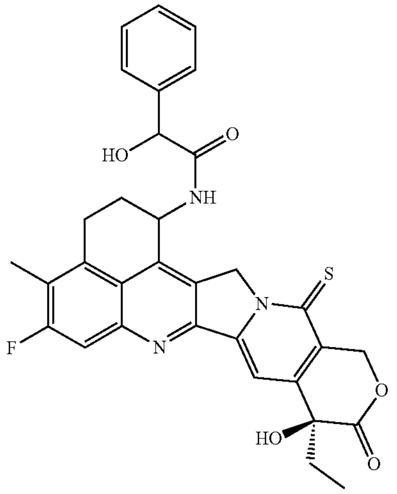
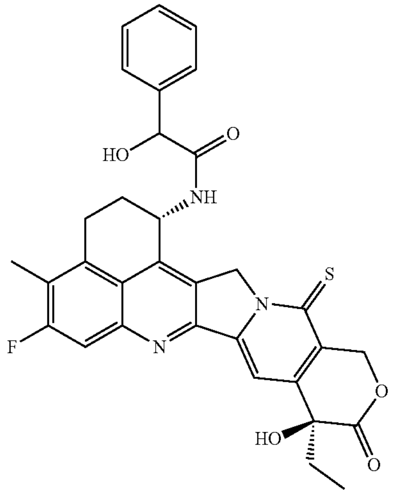
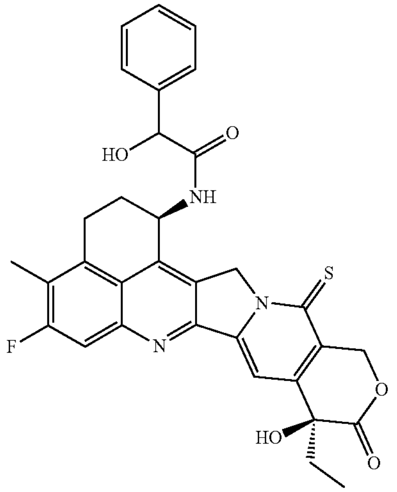

-continued
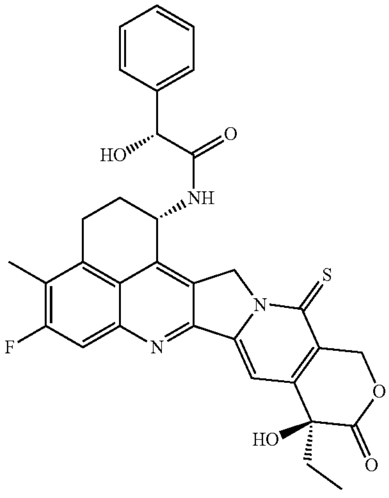
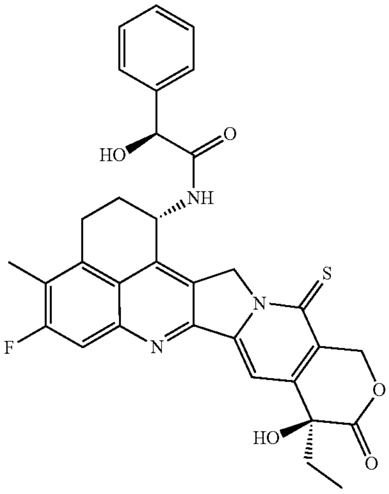
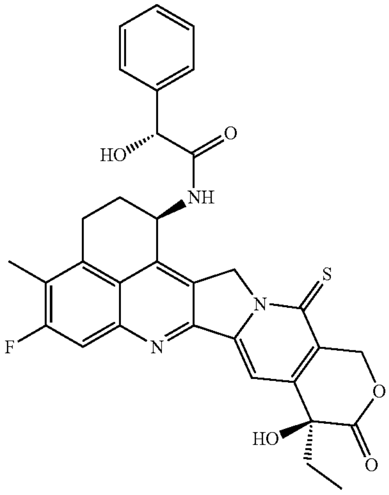
-continued
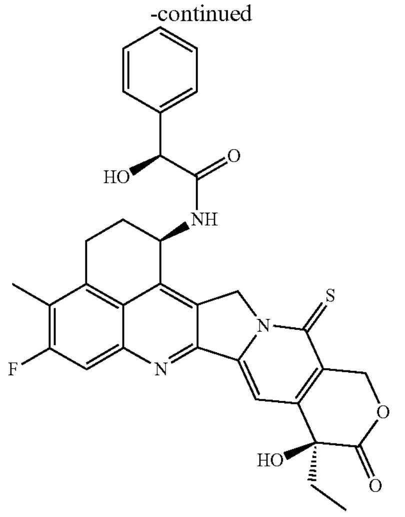
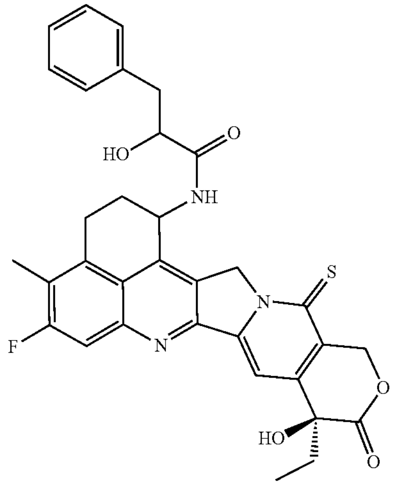
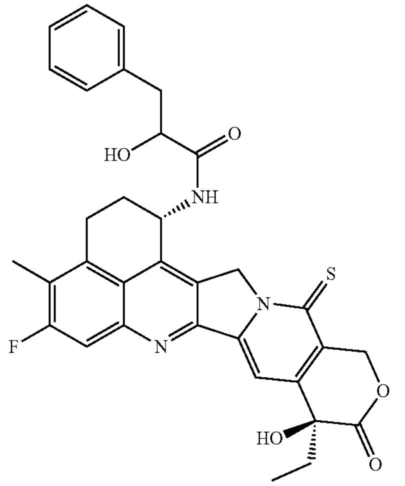

-continued
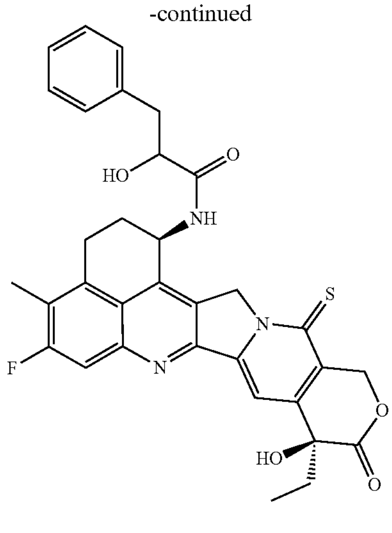
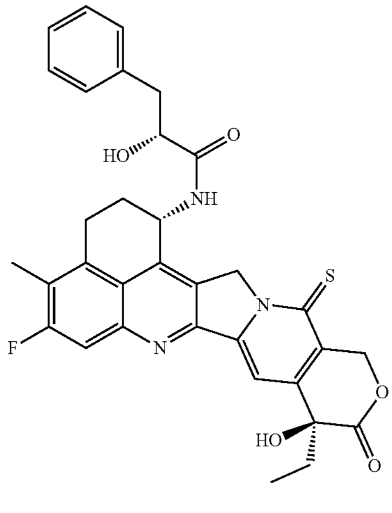
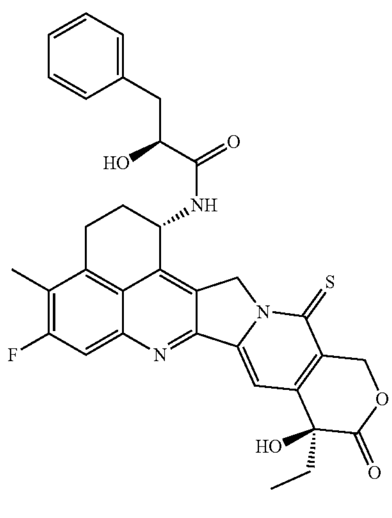
-continued
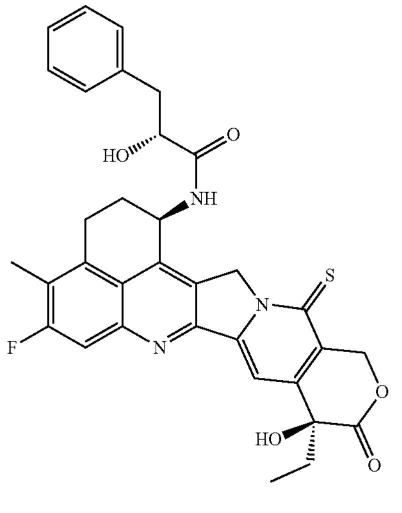
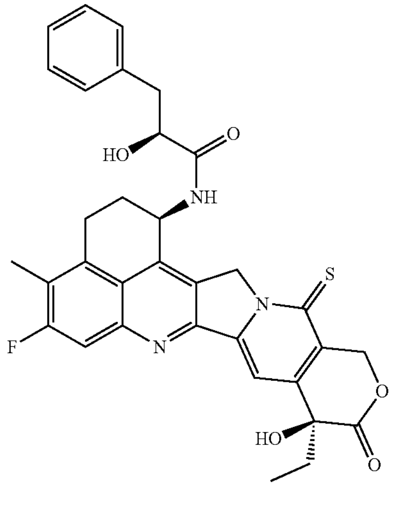
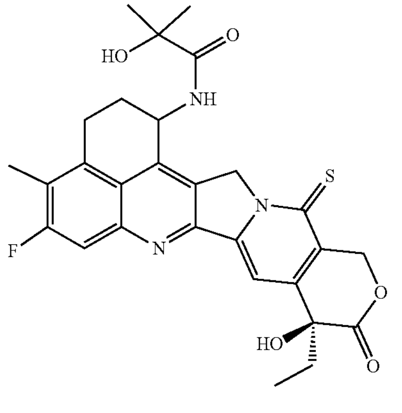

-continued
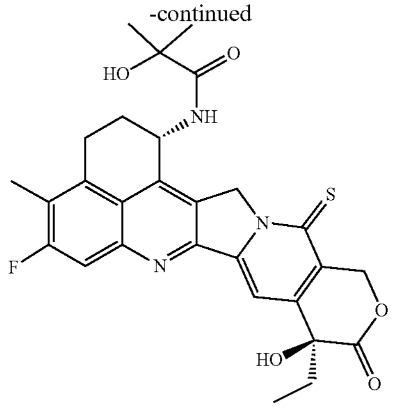
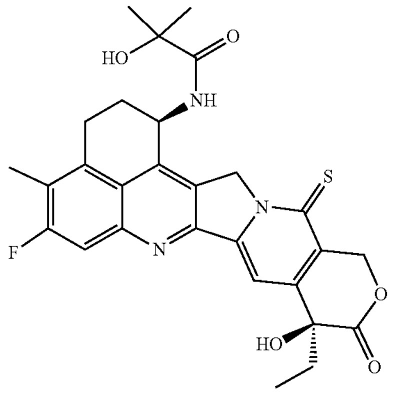
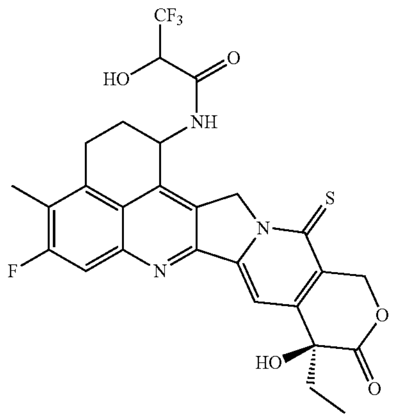
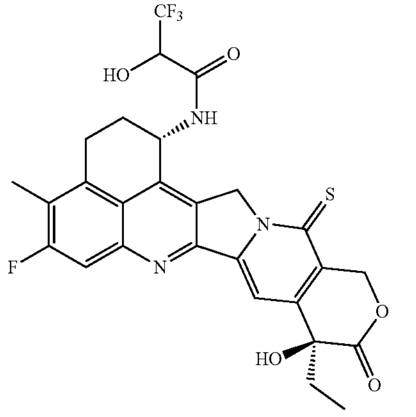
-continued
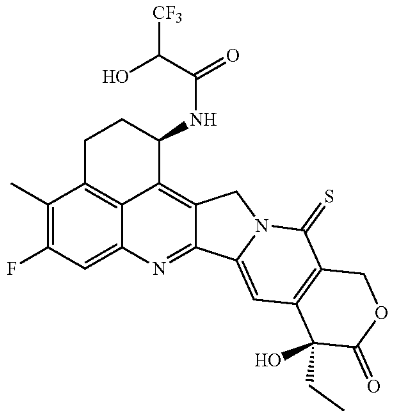
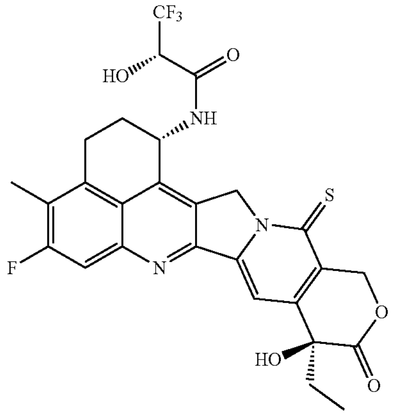
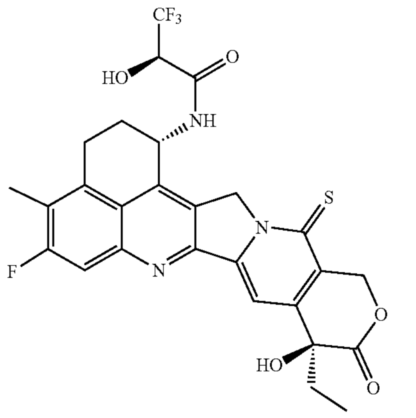
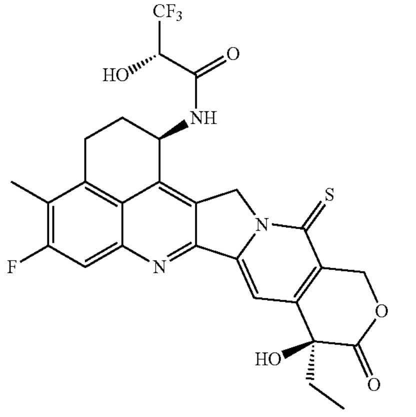

-continued
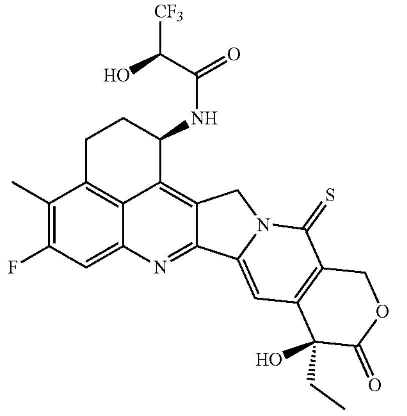
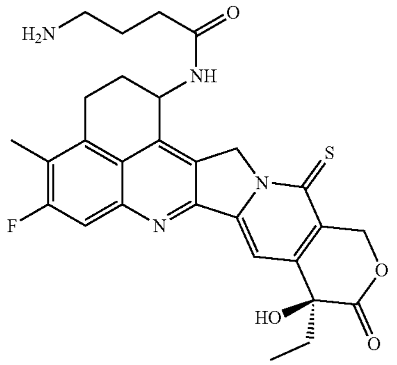
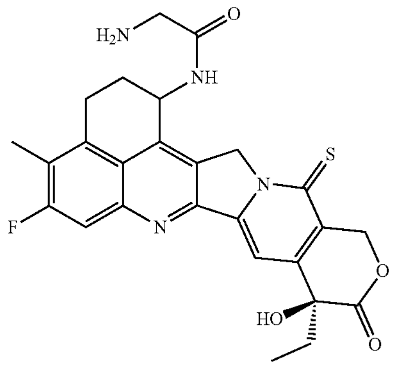
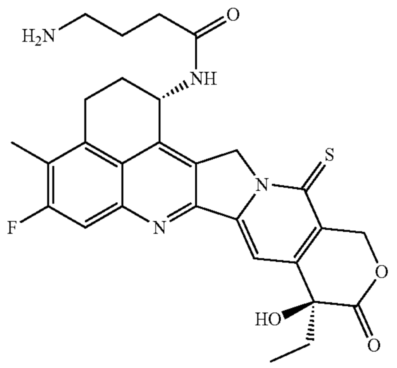
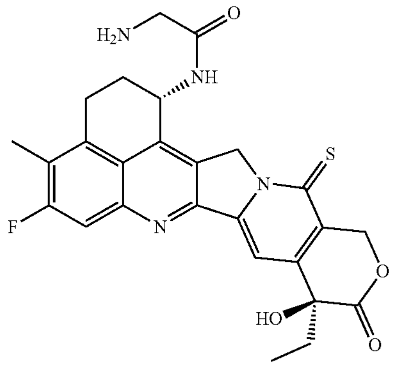
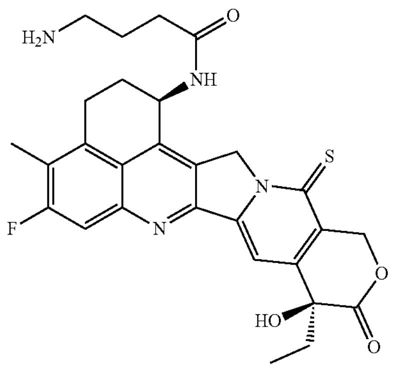
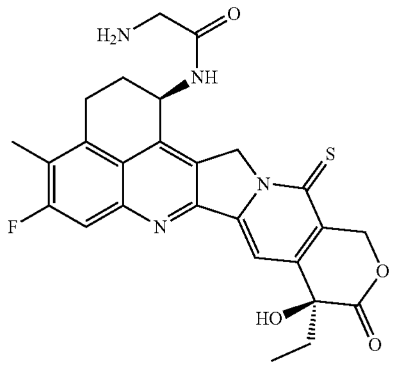
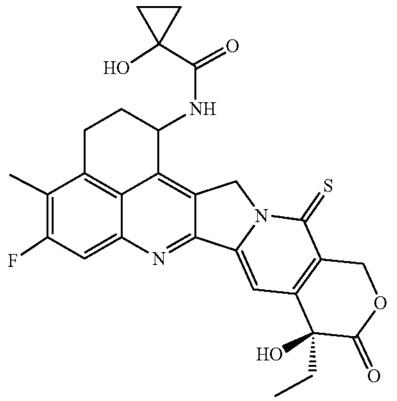

-continued
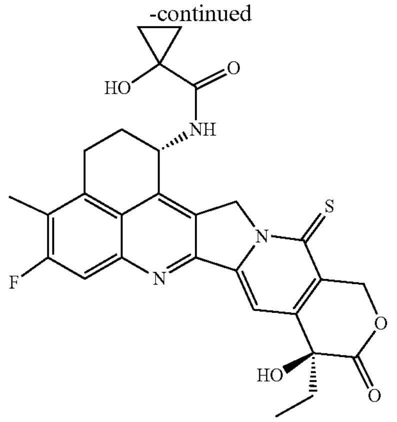
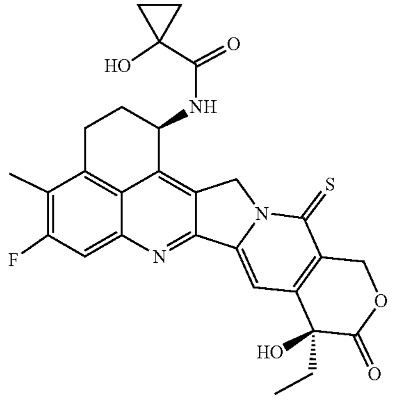
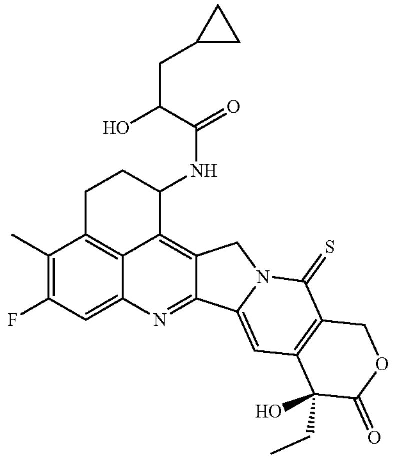
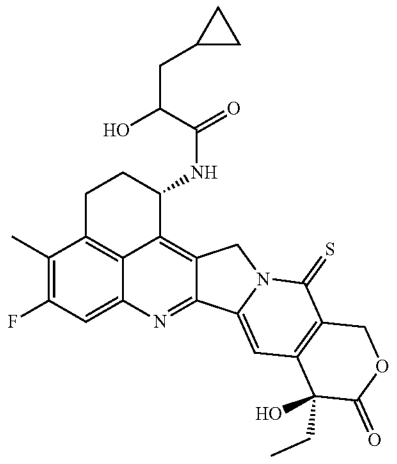
-continued
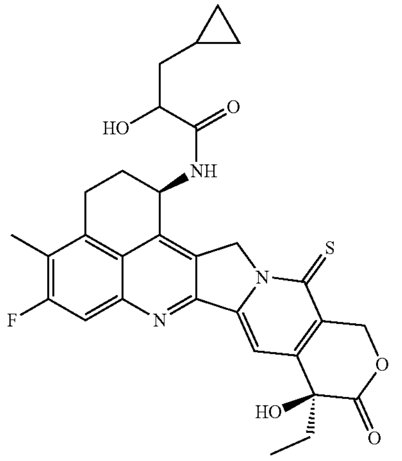
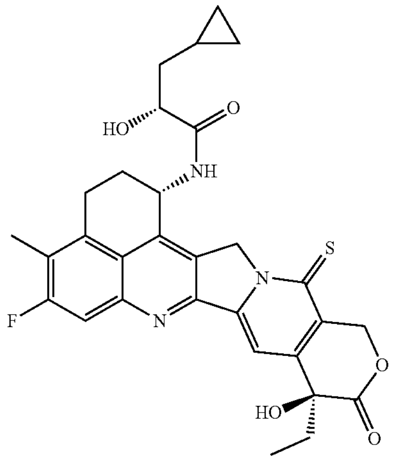
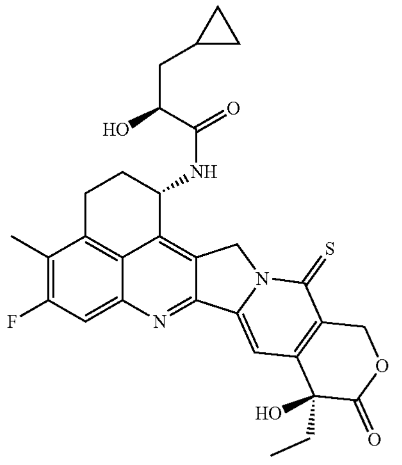

-continued
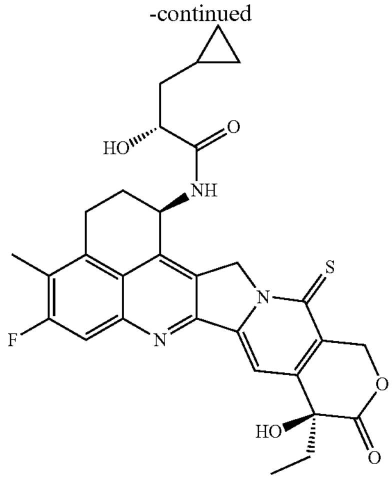
-continued
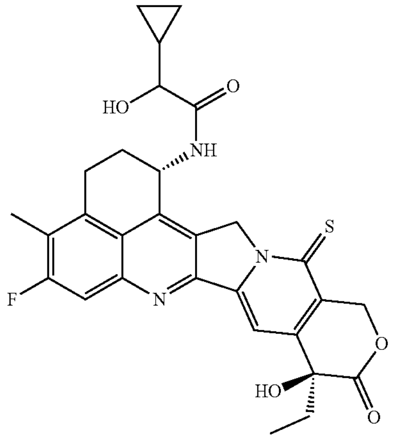
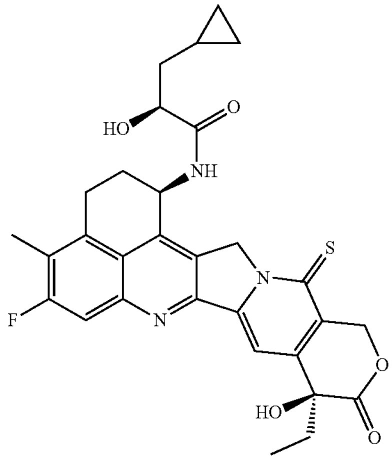
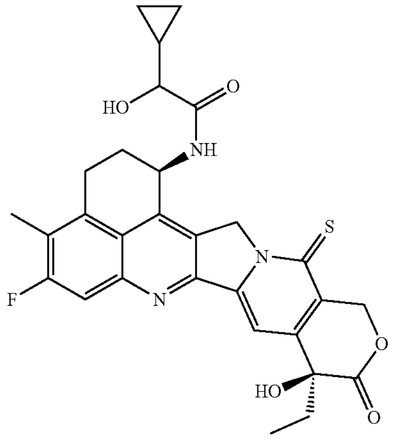
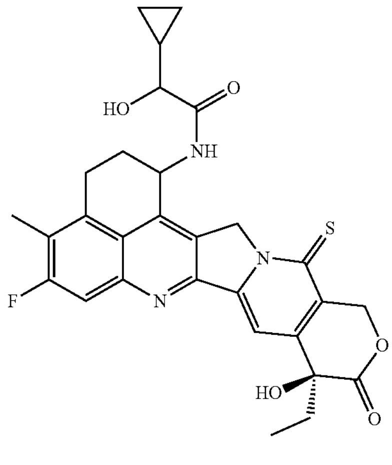
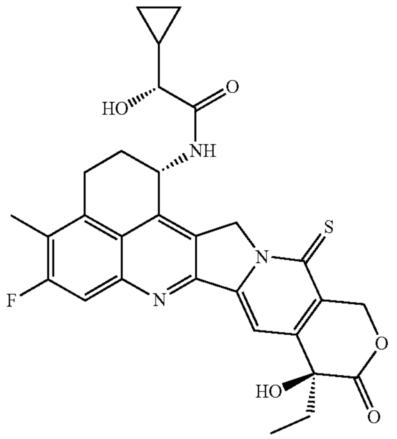

-continued

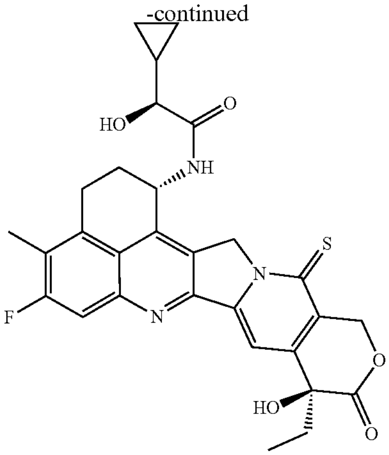

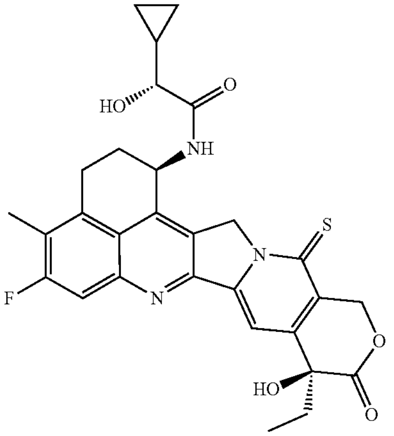

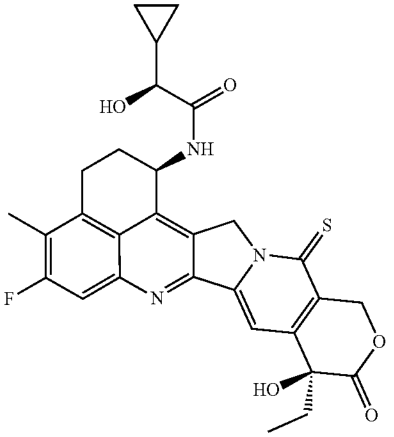

The second aspect of the present invention provides a pharmaceutical composition comprising a compound of formula I as described in any one of the first aspect of the present invention, or a pharmaceutically acceptable salt or a hydrate thereof, and one or more pharmaceutically acceptable excipients, diluents, or carriers.

The third aspect of the present invention provides a use of a compound of formula I as described in the first aspect of the present invention in the preparation of a pharmaceutical composition for treating diseases associated with tumor cell proliferation.

In another preferred embodiment, the disease is selected from the group consisting of breast cancer, ovarian cancer, cervical cancer, lung cancer, uterine cancer, prostate cancer, kidney cancer, urethral cancer, bladder cancer, liver cancer, stomach cancer, endometrial cancer, salivary gland cancer, esophageal cancer, melanoma, glioma, neuroblastoma, sarcoma, pharyngeal cancer, lung cancer, colon cancer, rectal cancer, colorectal cancer, leukemia, bone cancer, skin cancer, thyroid cancer, pancreatic cancer, and lymphoma.

The fourth aspect of the present invention provides a use of a compound of formula I as described in the first aspect of the present invention being used as a toxin in an antibody-drug conjugate in the preparation of an antibody-drug conjugate.

It should be understood that, in the present invention, each of the technical features specifically described above and below (such as those in the Examples) can be combined with each other, thereby constituting new or preferred technical solutions which are not necessarily specified one by one herein.

DETAILED DESCRIPTION OF THE INVENTION

After long-term and in-depth research, the inventor unexpectedly discovered a compound as shown in formula I. The compound has unexpected activity in inhibiting tumor cell proliferation and can be used to treat diseases associated with tumor cell proliferation. Based on the above findings, the inventors have completed the present invention.

Definition

As used herein, the term "alkyl" includes a linear or branched alkyl. For example, $C_1$-$C_8$ alkyl represents a linear or branched chain alkyl with 1-8 carbon atoms, such as methyl, ethyl, propyl, isopropyl, butyl, isobutyl, tert butyl, and the like.

As used herein, the term "alkenyl" includes a linear or branched chain alkenyl. For example, $C_2$-$C_6$ alkenyl refers to a linear or branched chain alkenyl with 2-6 carbon atoms, such as vinyl, allyl, 1-propenyl, isopropenyl, 1-butenyl, 2-butenyl, and the like.

As used herein, the term "alkynyl" includes a linear or branched chain alkynyl. For example, $C_2$-$C_6$ alkynyl refers to a straight or branched chain alkynyl with 2-6 carbon atoms, such as ethynyl, propynyl, butynyl, and the like.

As used herein, the term "$C_3$-$C_{10}$ cycloalkyl" refers to a cycloalkyl with 3-10 carbon atoms. It can be a single ring, such as cyclopropyl, cyclobutyl, cyclopentyl, cyclohexyl, and the like. It can also be bicyclic, such as a bridged ring or a spiro ring.

As used herein, the term "$C_1$-$C_8$ alkylamino" refers to anamino substituted by $C_1$-$C_8$ alkyl, which may be mono- or disubstituted; for example, methylamino, ethylamino, propylamino, ipropylamino, butylamino, isobutylamino, tert-butylamino, dimethylamino, diethylamino, dipropylamino, diisopropylamino, dibutylamino, diisobutylamino, di-tert-butylamino, etc.

As used herein, the term "$C_1$-$C_8$ alkoxy" refers to a linear or branched chain alkoxy with 1-8 carbon atoms; for example, methoxy, ethoxy, propoxy, isopropoxy, butoxy, iso-butyloxy, tert-butoxy, etc.

As used herein, the term "3-10 membered heterocycloalkyl with 1-3 heteroatoms selected from the group consisting of N, S, and O" refers to saturated or partially saturated cyclic group having 3-10 atoms and wherein 1-3 atoms are heteroatoms selected from N, S and O. It can be monocyclic, and it can also be bicyclic, such as a bridged ring or a spiro ring. Specific examples may be oxetanyl, azetidinyl, tetrahydro-2H-pyranyl, piperidinyl, tetrahydrofurfuryl, morpholinyl and pyrrolyl, etc.

As used herein, the term "$C_6$-$C_{10}$ aryl" refers to an aryl with 6-10 carbon atoms, e.g., phenyl or naphthyl and the like.

As used herein, the term "5-10 membered heteroaryl having 1-3 heteroatoms selected from the group consisting of N, S, and O" refers to a cyclic aromatic group having 5-10 atoms, and wherein 1-3 atoms are heteroatoms selected from N, S and O. It can be monocyclic, and it can also be fused. Specific examples may be pyridyl, pyridazinyl, pyrimidinyl, pyrazinyl, triazinyl, pyrrolyl, pyrazolyl, imidazolyl, (1,2,3)-triazolyl, and (1,2,4)-triazolyl, tetrazolyl, furyl, thienyl, isoxazolyl, thiazolyl, oxazolyl, etc.

Unless specifically stated, the groups described in the present invention are "substituted or unsubstituted", the groups of the present invention can be substituted by substituents selected from the group consisting of halogen, cyano, nitro, hydroxyl, amino, $C_1$-$C_6$ alkyl-amino, $C_1$-$C_6$ alkyl, $C_2$-$C_6$ alkenyl, $C_2$-$C_6$ alkynyl, $C_1$-$C_6$ alkoxy, halogenated $C_1$-$C_6$ alkyl, halogenated $C_2$-$C_6$ alkenyl, halogenated $C_2$-$C_6$ alkynyl, halogenated $C_1$-$C_6$ alkoxy, allyl, benzyl, $C_6$-$C_{12}$ aryl, $C_1$-$C_6$ alkoxy-$C_1$-$C_6$ alkyl, $C_1$-$C_6$ alkoxy-carbonyl, phenoxycarbonyl, $C_2$-$C_6$ alkynyl-carbonyl, $C_2$-$C_6$ alkenyl-carbonyl, $C_3$-$C_6$ cycloalkyl-carbonyl, $C_1$-$C_6$ alkyl-sulfonyl, etc.

As used herein, "halogen" or "halogen atom" refers to F, Cl, Br, and I. More preferably, the halogen or halogen atom is selected from F, Cl, and Br. "Halogenated" refers to being replaced by an atom selected from F, Cl, Br, and I.

Unless otherwise specified, the structural formula described in the invention is intended to include all isomeric forms (such as enantiomers, diastereomers and geometric isomers (or conformational isomers)): for example, R and S configurations of asymmetric centers, (Z) and (E) isomers of double bonds, etc. Therefore, a single stereochemical isomer of the compound of the invention or a mixture of its enantiomers, diastereomers or geometric isomers (or conformational isomers) is within the scope of the invention.

As used herein, the term "tautomer" means that structural isomers with different energies can cross the low energy barrier and transform into each other. For example, proton tautomer (i.e. proton shift) include in interconversion through proton migration, such as 1H-indazole and 2H-indazole. The valence tautomer involves interchange through some bonding electron recombination.

As used herein, the term "hydrate" refers to a complex formed by the coordination of a compound of the present invention with water.

The compound of this application can be prepared through various synthetic methods well-known to those skilled in the art, including the specific embodiments listed below, the embodiments formed by combining the specific embodiments with other chemical synthesis methods, and equivalent substitution methods well-known for those skilled in the art. Preferred embodiments include but are not limited to the embodiments of this application.

The solvent used in this application are commercially available, compounds are named manually or by ChemDraw® software, and commercially available compounds are named by supplier catalog.

Preparation of Compounds

The compounds of the present invention can be prepared by the following general methods:

Preparation Method 1:

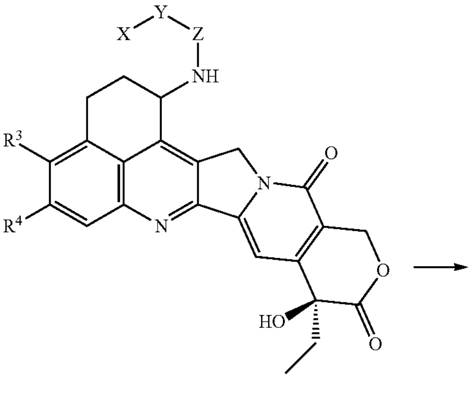

Ia

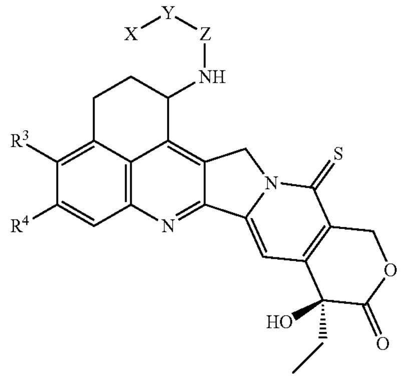

I

Reacting a compound of formula Ia with phosphorus pentasulfide or Lawesson's reagent to obtain a compound of formula I.

Preparation Method 2:

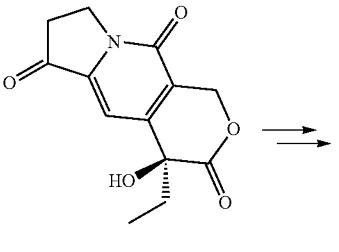

IIa

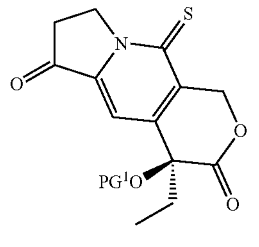

IIc

-continued

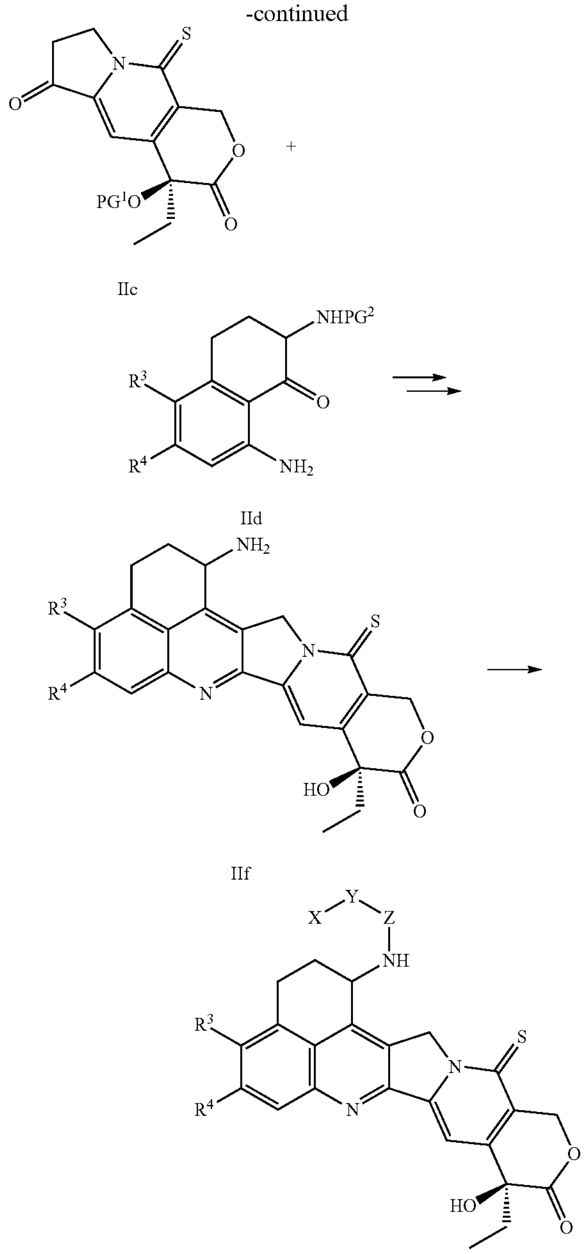

IIc

IId

IIf

I

Protecting the hydroxyl group in the compound of formula Ha with protecting group ($PG^1$), and then reacting with phosphorus pentasulfide or Lawesson's reagent to obtain compound of formula IIc. Then compound of formula IIc and IId undergo dehydration condensation and deprotection ($PG^1$ and $PG^2$) reaction to obtain compound of formula IIf. Finally, the compound of formula I was obtained by the conversion of compound of formula IIf.

Pharmaceutical Composition and Method of Administration

Since the compound of the present invention has excellent inhibitory activity against tumor cell proliferation, the compound of the present invention and its various crystal forms, pharmaceutically acceptable inorganic or organic salts, hydrates or solvates, and the pharmaceutical composition containing the compound of the present invention as the main active ingredient can be used to prevent and/or treat (stabilize, alleviate or cure) diseases associated with tumor cell proliferation.

The pharmaceutical composition of the present invention comprises a safe and effective amount of the compound of the present invention and a pharmaceutically acceptable excipient or carrier. Wherein "safe and effective amount" refers to the amount of compound is sufficient to significantly improve the condition, not to produce severe side effects. Typically, the pharmaceutical composition contains 1-2000 mg of the compound/dosage of the present invention, and preferably contains 1-200 mg of the compound/dosage of the present invention. Preferably, "one dosage" is a capsule or a pill.

"Pharmaceutically acceptable carrier" refers to one or more compatible solid or liquid filler or gel substances, which are suitable for human use, and must be sufficiently pure and sufficiently low toxicity. "Compatible" herein refers to the ability of each component of a composition can be mixed with the compound of the present invention and can be mixed with each other without appreciably reducing the efficacy of the compound. Examples of pharmaceutically acceptable carrier include cellulose and derivatives thereof (such as sodium carboxymethylcellulose, sodium ethylcellulose, cellulose acetate, etc.), gelatin, talc, solid lubricant (such as stearic acid, magnesium stearate), calcium sulfate, vegetable oil (such as soybean oil, sesame oil, peanut oil, olive oil, etc.), polyol (such as propylene glycol, glycerol, mannitol, sorbitol, etc.), emulsifier (such as Tween®), wetting agent (such as lauryl sodium sulfate), colorant, flavoring, stabilizer, antioxidant, preservative, pyrogen-free water, etc.

There is no special limitation of administration mode for the compound or pharmaceutical compositions of the present invention, and the representative administration mode includes (but is not limited to) oral, parenteral (intravenous, intramuscular or subcutaneous).

Solid dosage forms for oral administration include capsules, tablets, pills, powders and granules. In these solid dosage forms, the active compounds are mixed with at least one conventional inert excipient (or carrier), such as sodium citrate or di-calcium phosphate, or mixed with any of the following components: (a) fillers or compatibilizer, such as starch, lactose, sucrose, glucose, mannitol and silicic acid; (b) binders, such as hydroxyl methyl cellulose, alginate, gelatin, polyvinyl pyrrolidone, sucrose and arabic gum; (c) humectant, such as, glycerol; (d) disintegrating agent, such as agar, calcium carbonate, potato starch or tapioca starch, alginic acid, certain composite silicates, and sodium carbonate; (e) dissolution-retarding agents, such as paraffin; (f) absorption accelerators, such as quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, lauryl sodium sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, such as ethanol, isopropanol, ethyl carbonate, ethyl acetate, propylene glycol, 1,3-butanediol, dimethylformamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The compounds of the present invention may be administered alone or in combination with other pharmaceutically acceptable therapeutic agents.

When administered in combination, the pharmaceutical composition also includes one or more (2, 3, 4, or more) other pharmaceutically acceptable therapeutic agents. One or more (2, 3, 4, or more) of the other pharmaceutically acceptable therapeutic agents may be used simultaneously, separately or sequentially with the compounds of the present invention for the prevention and/or treatment of diseases related to cytokine and/or interferon.

When the pharmaceutical composition is used, a safe and effective amount of the compound of the present invention is applied to a mammal (such as a human) in need of treatment, wherein the dose is considered as a pharmaceutically effective dose. For a person weighing 60 kg, the daily dose is usually 1 to 2000 mg, preferably 1 to 500 mg. Of course, the particular dose should also depend on various factors, such as the route of administration, patient healthy status, which are well within the skills of an experienced physician.

The present invention will be further illustrated below with reference to the specific examples. It should be understood that these examples are only to illustrate the invention but not to limit the scope of the invention. The experimental methods in which conditions have not been specified in the following examples are usually based on conventional conditions, or in accordance with methods recommended by the manufacturer. Percentages and servings are by weight unless otherwise noted.

EXAMPLES

Example 1

1-1

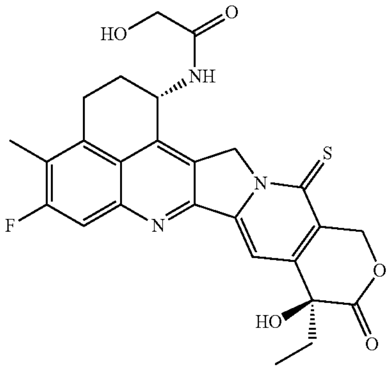

1-2

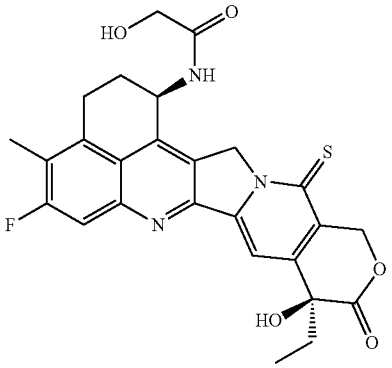

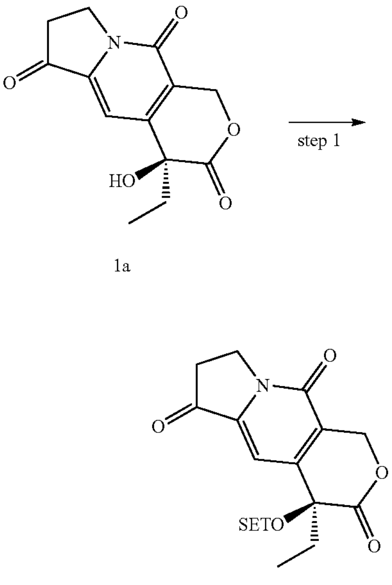

1a 1b-1

+

-continued

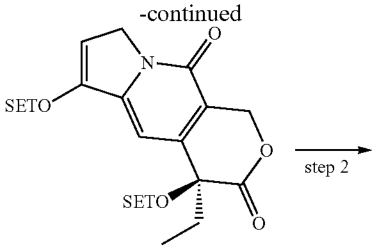

1b-2

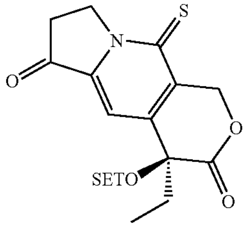

1c

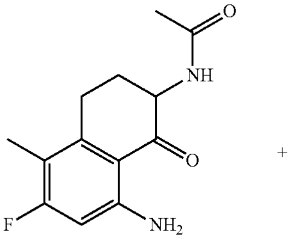

1d

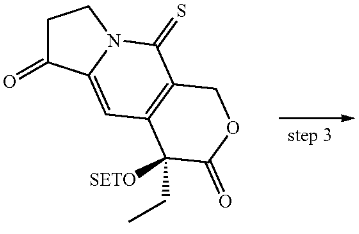

1c

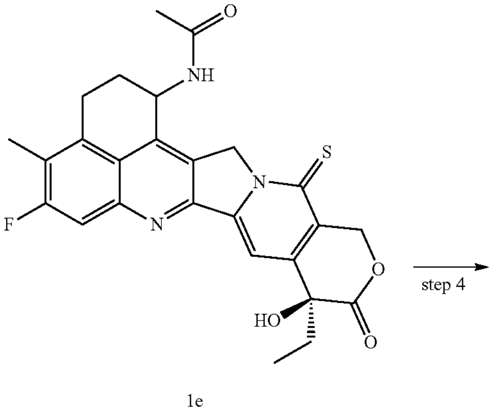

1e

-continued

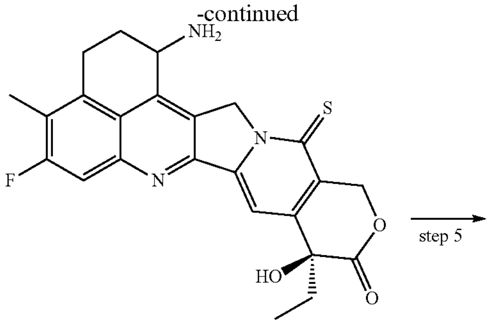

1f

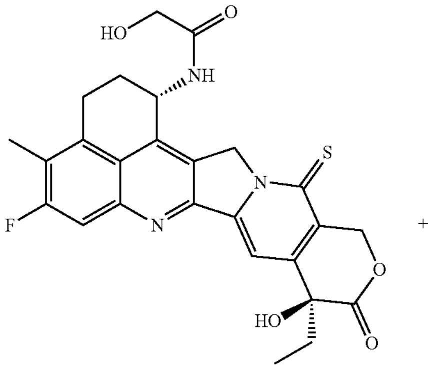

1-1

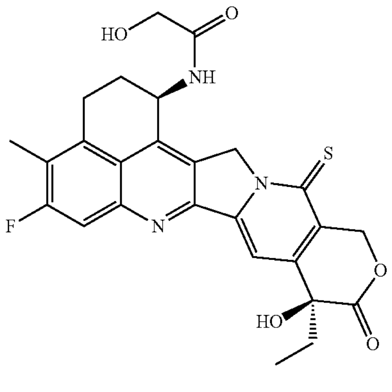

1-2

Step 1

1a (1.95 g, 7.40 mmol), imidazole (2.52 g, 37.00 mmol) were added to a three-neck round-bottom flask (100 mL), the mixture was degassed under vacuum and purged with $N_2$, anhydrous N,N-dimethylformamide (30 mL) was added to the mixture, the reaction mixture was cooled down to 0° C. in an ice-water bath, followed by the addition of chlorotriethylsilane (4.45 g, 29.60 mmol) and 4-dimethylaminopyridine (0.90 g, 7.40 mmol), the resulting mixture was stirred at 0° C. for 2 h. Ethyl acetate (200 mL) was added to the mixture. The organic phase was washed with brine (25 mL×4), dried over anhydrous sodium sulfate and the dried solution was filtrated.

The filtrate was concentrated and the residue was purified by flash column chromatography on silica gel (ethyl acetate: hexanes=0-100%) to give 1b-1 (0.90 g), 1b-2 (1.50 g) with 73% yield.

1b-1:

MS-ESI calc. for $C_{19}H_{28}NO_5Si$ $[M+H]^+$378, found 378.

1b-2:

MS-ESI calc. for $C_{25}H_{42}NO_5Si_2$ $[M+H]^+$492, found 378 (lose one TES).

Step 2

1b-2 (1.10 g, 2.20 mmol), Lawesson's Reagent (1.80 g, 4.40 mmol) were added to a three-neck round-bottom flask (100 mL) the mixture was degassed under vacuum and purged with $N_2$, anhydrous toluene (30 mL) was added to the mixture, the resulting mixture was stirred at 90° C. for 5-6 h. Ethyl acetate (200 mL) was added to the mixture, the obtained solution was washed with brine (25 mL×2). The organic phase was dried over anhydrous sodium sulfate and the dried solution was filtrated. The filtrate was concentrated and the residue was purified by flash column chromatography on silica gel (ethyl acetate:hexanes=0-100%) to give 1c (620 mg) with 51% yield.

MS-ESI calc. for $C_{19}H_{28}NO_4SSi$ $[M+H]^+$394, found 394.

Step 3

To a round-bottom flask (100 mL) were added 1c (620 mg, 1.10 mmol), 1d (380 mg, 1.54 mmol) and pyridinium 4-toluenesulfonate (166 mg, 0.66 mmol), toluene was added to the mixture (30 mL), the mixture was degassed under vacuum and purged with $N_2$, the resulting mixture was stirred at 120° C. for 24 h, another batch of 1d (60 mg) and pyridinium 4-toluenesulfonate (90 mg) were added and the mixture was stirred at 120° C. for additional 20 h. The reaction mixture was cooled to room temperature, evaporated and the residue was purified by flash column chromatography on silica gel (MeOH:DCM=0-100%) to give 1e (260 mg) with 48% yield.

MS-ESI calc. for $C_{26}H_{25}FN_3O_4S$ $[M+H]^+$494, found 494.

Step 4

To a round-bottom flask (100 mL) were added 1e (80 mg, 0.16 mmol), $HCl_{(aq)}$ (6 N, 27 mL) was added to the mixture, the reaction mixture was stirred at 110° C. for 4 h. The reaction mixture was cooled down to room temperature and filtered, the filtrate was concentrated to give crude product 1f (50 mg).

MS-ESI calc. for $C_{24}H_{23}FN_3O_3S$ $[M+H]^+$452, found 452.

Step 5

To a round-bottom flask (25 mL) were added 1f (20 mg, 0.04 mmol) and a solution of glycolic acid in N,N-dimethylformamide (2.00 mL, 0.032 mmol, 1.2 mg/mL), the mixture was cooled down to 0° C. followed by addition of N,N-diisopropylethylamine (11 mg, 0.08 mmol) and O-(7-azabenzotriazol-1-yl)-N,N,N',N'-tetramethyluroniumhexafluorophosphate (16 mg, 0.04 mmol), the reaction mixture was stirred for 0.5 h. Another batch of solution of glycolic acid in N,N-dimethylformamide (0.20 mL, 0.003 mmol) and O-(7-azabenzotriazol-1-yl)-N, N,N',N'-tetramethyluroniumhexafluorophosphate (1 mg) were added, the reaction mixture was stirred for additional 1 h. Ethyl acetate (80 mL) was added to the reaction mixture. The organic phase was washed by $HCl_{(aq)}$(0.5 N, 5 mL×1), saturated aqueous sodium bicarbonate (10 mL×2) and brine (10 mL×5). The organic phase was dried over anhydrous sodium sulfate and the dried solution was filtrated. The filtrate was concentrated and the residue was purified by Prep-TLC (MeOH:DCM) to give 1-1 (2 mg) and 1-2 (5 mg) with 34% yield.

1-1:

MS-ESI calc. for $C_{26}H_{25}FN_3O_5S$ $[M+H]^+$510, found 510.

$^1H$ NMR (400 MHz, DMSO-$d_6$) δ 8.54 (d, J=8.8 Hz, 1H), 7.82 (d, J=10.8 Hz, 1H), 7.80 (s, 1H), 5.92 (d, J=16.8 Hz, 1H), 5.69-5.60 (m, 1H), 5.53 (d, J=20.4 Hz, 1H), 5.52 (d, J=16.4 Hz, 1H), 5.35 (d, J=20.0 Hz, 1H), 4.15-3.98 (m, 2H), 3.30-3.22 (m, 1H), 3.19-3.09 (m, 1H), 2.40 (s, 3H), 2.26-2.14 (m, 2H), 1.96-1.84 (m, 2H), 0.86 (t, J=7.2 Hz, 3H).

1-2:

MS-ESI calc. for $C_{26}H_{25}FN_3O_5S$ $[M+H]^+$510, found 510.

$^1H$ NMR (400 MHz, DMSO-$d_6$) δ 8.54 (d, J=9.2 Hz, 1H), 7.81 (d, J=11.2 Hz, 1H), 7.80 (s, 1H), 6.69 (s, 1H), 5.92 (d, J=16.8 Hz, 1H), 5.69-5.62 (m, 1H), 5.62-5.56 (m, 1H), 5.55-5.47 (m, 2H), 5.33 (d, J=20.0 Hz, 1H), 4.16-3.98 (m, 2H), 3.30-3.20 (m, 1H), 3.16-3.07 (m, 1H), 2.39 (s, 3H), 2.26-2.15 (m, 2H), 1.95-1.85 (m, 2H), 0.86 (t, J=7.2 Hz, 3H).

Example 2

2-1

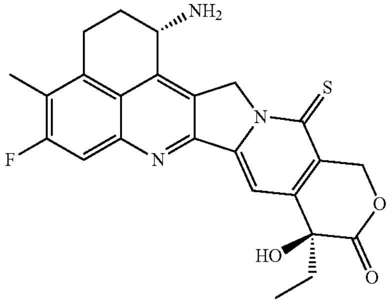

2-2

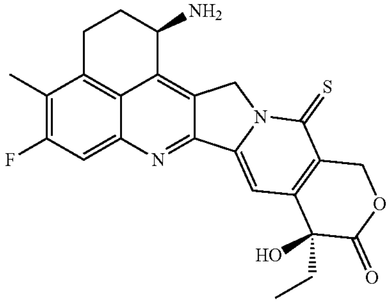

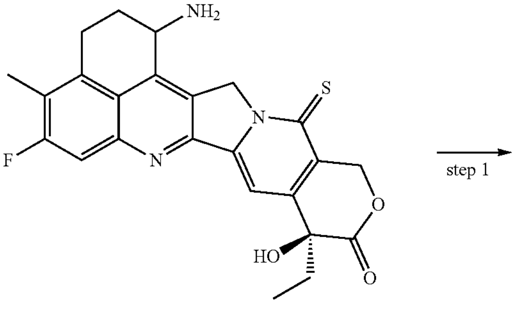

1f

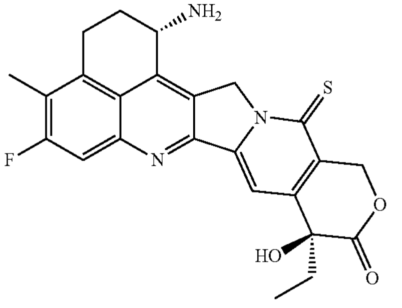

+

2-1

-continued

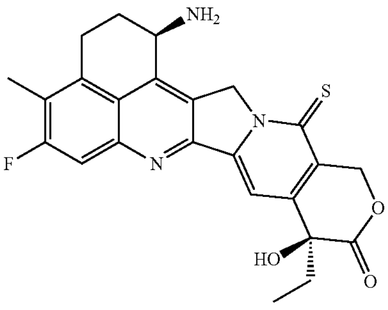

2-2

Step 1

The crude product 1f (15.00 g) was purified by Prep-HPLC to give 2-1 (2.80 g) and 2-2 (4.00 g) with 45% yield.

2-1:

MS-ESI calc. for $C_{24}H_{23}FN_3O_3S$ $[M+H]^+$452, found 452.

$^1$H NMR (400 MHz, DMSO-$d_6$) δ 7.82-7.73 (m, 2H), 6.70 (s, 1H), 5.92 (d, J=16.8 Hz, 1H), 5.86 (d, J=20.4 Hz, 1H), 5.59 (d, J=20.4 Hz, 1H), 5.52 (d, J=16.4 Hz, 1H), 4.45-4.37 (m, 1H), 3.30-3.19 (m, 1H), 3.10-2.98 (m, 1H), 2.40 (s, 3H), 2.25-2.12 (m, 1H), 2.08-1.96 (m, 1H), 1.95-1.82 (m, 2H), 0.86 (t, J=7.2 Hz, 3H).

2-2:

MS-ESI calc. for $C_{24}H_{23}FN_3O_3S$ $[M+H]^+$452, found 452.

$^1$H NMR (400 MHz, DMSO-$d_6$) δ 8.51 (d, J=4.4 Hz, 1H), 7.92 (d, J=10.4 Hz, 1H), 7.84 (s, 1H), 6.02 (d, J=20.0 Hz, 1H), 5.95 (d, J=16.4 Hz, 1H), 5.70 (d, J=20.0 Hz, 1H), 5.53 (d, J=16.8 Hz, 1H), 5.23-5.15 (m, 1H), 3.36-3.25 (m, 1H), 3.20-3.07 (m, 1H), 2.60-2.51 (m, 1H), 2.42 (s, 3H), 2.25-2.12 (m, 1H), 1.98-1.82 (m, 1H), 0.86 (t, J=7.2 Hz, 3H).

Example 3

3

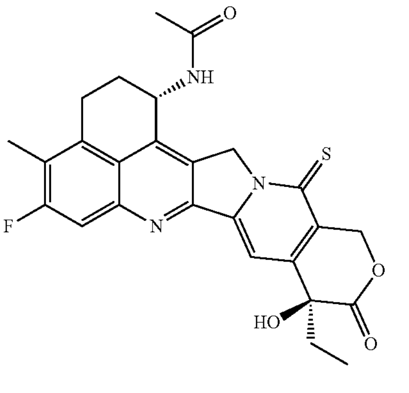

-continued

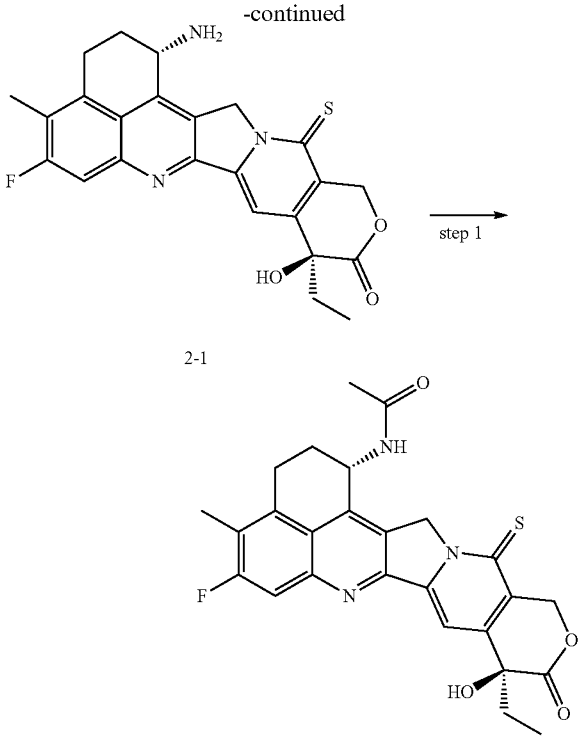

2-1

3

Step 1

To a round-bottom flask (25 mL) were added 2-1 (20 mg, 0.04 mmol), DCM (2 mL) and triethylamine (25 μL, 0.18 mmol), acetic anhydride was added dropwise to the solution (19 μL, 0.20 mmol), the resulting mixture was stirred at room temperature for 1 h. The reaction mixture was filtrated, the filter cake was washed with DCM (5 mL), the solid was collected and dried to give 3 (10 mg) with 46% yield.

MS-ESI calc. for $C_{26}H_{25}FN_3O_4S$ $[M+H]^+$494, found 494.

$^1$H NMR (400 MHz, DMSO-$d_6$) δ 8.59 (d, J=8.8 Hz, 1H), 7.84 (d, J=10.8 Hz, 1H), 7.79 (s, 1H), 6.71 (s, 1H), 5.91 (d, J=16.8 Hz, 1H), 5.62-5.57 (m, 1H), 5.56-5.48 (m, 2H), 5.41 (d, J=20.0 Hz, 1H), 3.26-3.12 (m, 2H), 2.41 (s, 3H), 2.22-2.10 (m, 2H), 2.00 (s, 3H), 1.92-1.86 (m, 2H), 0.85 (t, J=7.2 Hz, 3H).

Example 4

4

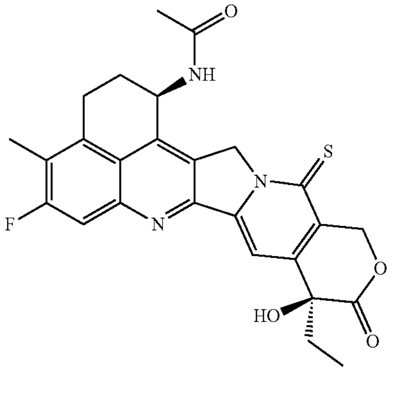

-continued

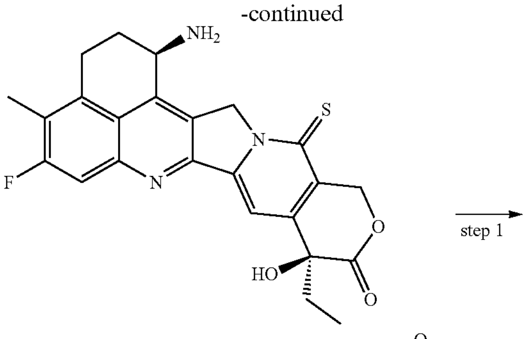

2-2

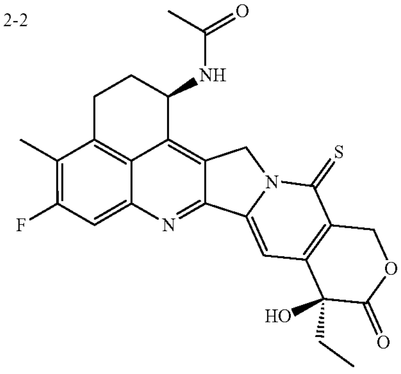

4

Step 1

To a round-bottom flask (100 mL) were added 2-2 (4.00 g, 8.86 mmol), anhydrous DCM (30 mL) and triethylamine (3.58 g, 35.44 mmol), acetic anhydride was added dropwise to the solution (3.70 g, 36.28 mmol), the resulting mixture was stirred at room temperature for 1.5 h. the reaction mixture was filtrated, the filter cake was washed with DCM (20 mL), the solid was collected and dried to give 4 (4.26 g) with 96% yield.

MS-ESI calc. for $C_{26}H_{25}FN_3O_4S$ $[M+H]^+$494, found 494.

$^1$H NMR (400 MHz, DMSO-$d_6$) δ 8.58 (d, J=8.8 Hz, 1H), 7.83-7.77 (m, 2H), 6.70 (s, 1H), 5.91 (d, J=16.8 Hz, 1H), 5.61-5.55 (m, 1H), 5.55-5.51 (m, 1H), 5.49 (d, J=12.0 Hz, 1H), 5.32 (d, J=19.6 Hz, 1H), 3.28-3.07 (m, 2H), 2.37 (s, 3H), 2.26-2.04 (m, 2H), 2.01 (s, 3H), 1.96-1.84 (m, 2H), 0.88 (t, J=7.2 Hz, 3H).

Example 5

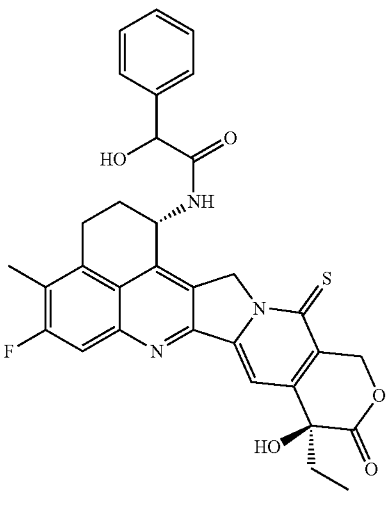

5

-continued

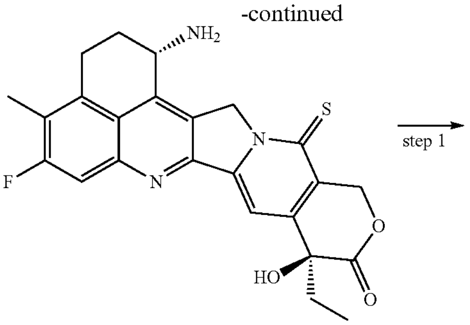

2-1

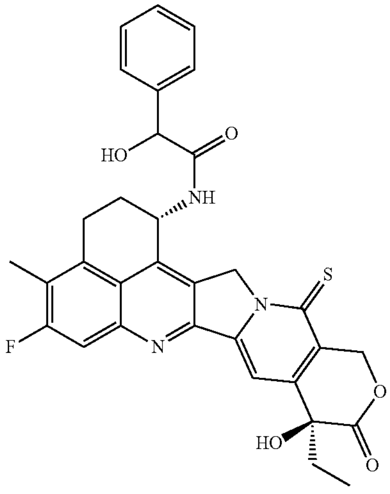

5

Step 1

To a round-bottom flask (25 mL) were added 2-1 (20 mg, 0.04 mmol), 2-hydroxy-2-phenylacetic acid (13 mg, 0.09 mmol) and N,N-dimethylformamide (2 mL), N,N-diisopropylethylamine (21 μL, 0.12 mmol) and O-(7-azabenzotriazol-1-yl)-N,N,N',N'-tetramethyluroniumhexafluorophosphate (23 mg, 0.06 mmol) were then added, the resulting mixture was stirred at room temperature for 1.5 h. $H_2O$ (50 mL) was added to the reaction mixture. The aqueous phase was extracted with DCM/MeOH ($V_{DCM}$:$V_{MeOH}$=10:1, 15 mL×4). The combined organic phases were dried over anhydrous sodium sulfate and the dried solution was filtrated. The filtrate was concentrated and the residue was purified by Prep-TLC (MeOH:DCM) to give 5 (5 mg) with 19% yield.

MS-ESI calc. for $C_{32}H_{29}FN_3O_5S$ $[M+H]^+$586, found 586.

$^1$H NMR (400 MHz, DMSO-$d_6$) δ 8.76-8.70 (m, 1H), 7.88-7.82 (m, 1H), 7.803 (s, 0.5H), 7.800 (s, 0.5H), 7.56 (d, J=7.2 Hz, 1H), 7.46 (d, J=6.8 Hz, 1H), 7.35-7.31 (m, 2H), 7.29-7.26 (m, 1H), 6.72 (s, 1H), 6.33-6.18 (m, 1H), 5.93 (d, J=16.8 Hz, 0.5H), 5.92 (d, J=16.4 Hz, 0.5H), 5.56-5.47 (m, 4H), 5.17-5.02 (m, 1H), 3.17-3.13 (m, 2H), 2.41 (s, 3H), 2.17-2.10 (m, 2H), 1.94-1.87 (m, 2H), 0.87 (t, J=7.2 Hz, 3H).

Example 6

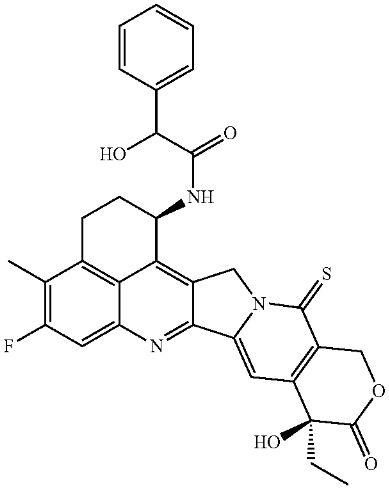

6

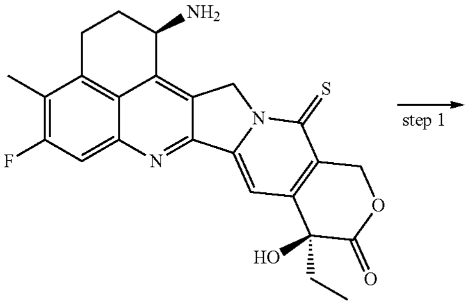

2-2

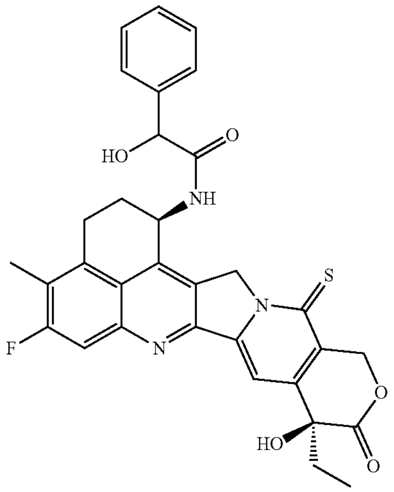

6

Step 1

To a round-bottom flask (25 mL) were added 2-2 (60 mg, 0.13 mmol), 2-hydroxy-2-phenylacetic acid (40 mg, 0.27 mmol) and N,N-dimethylformamide (2 mL), N,N-diisopropylethylamine (52 mg, 0.40 mmol) and O-(7-azabenzotriazol-1-yl)-N,N,N',N'-tetramethyluroniumhexafluorophosphate (76 mg, 0.20 mmol) were then added, the resulting mixture was stirred at room temperature for 1.5 h. $H_2O$ (10 mL) was added to the reaction mixture. The aqueous phase was extracted with ethyl acetate (200 mL×1). The organic phase was washed with brine (25 mL×4) and dried over anhydrous sodium sulfate. The dried solution was filtrated. The filtrate was concentrated and the residue was purified by Prep-TLC (MeOH:DCM) to give 6 (65 mg) with 83% yield.

MS-ESI calc. for $C_{32}H_{29}FN_3O_5S$ $[M+H]^+$586, found 586.

$^1$H NMR (400 MHz, DMSO-$d_6$) δ 8.80-8.70 (m, 1H), 7.87-7.81 (m, 1H), 7.81 (s, 0.5H), 7.80 (s, 0.5H), 7.57 (d, J=7.2 Hz, 1H), 7.46 (d, J=7.2 Hz, 1H), 7.37-7.30 (m, 2H), 7.30-7.23 (m, 1H), 6.71 (s, 1H), 6.35-6.17 (m, 1H), 5.95 (d, J=16.4 Hz, 0.5H), 5.93 (d, J=16.4 Hz, 0.5H), 5.65-5.35 (m, 4H), 5.15-5.02 (m, 1H), 3.22-3.06 (m, 2H), 2.39 (s, 3H), 2.19-2.05 (m, 2H), 1.96-1.85 (m, 2H), 0.87 (t, J=7.2 Hz, 3H).

Example 7

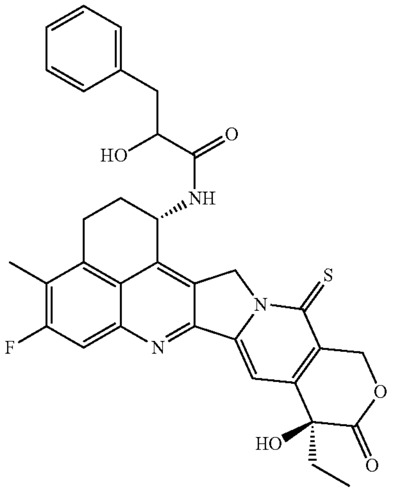

7

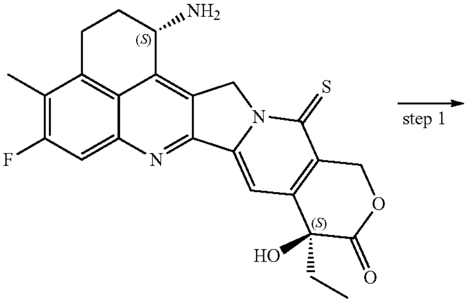

2-1

-continued

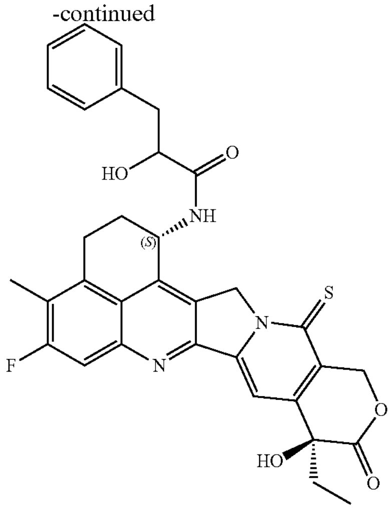

7

Step 1

To a round-bottom flask (25 mL) were added 2-1 (20 mg, 0.04 mmol), 2-hydroxy-3-phenylacetic acid (15 mg, 0.09 mmol) and N,N-dimethylformamide (2 mL), N,N-diisopropylethylamine (21 μL, 0.12 mmol) and O-(7-azabenzotriazol-1-yl)-N,N,N',N'-tetramethyluroniumhexafluorophosphate (23 mg, 0.06 mmol) were then added, the resulting mixture was stirred at room temperature for 1.5 h. $H_2O$ (50 mL) was added to the reaction mixture. The aqueous phase was extracted with DCM/MeOH ($V_{DCM}$:$V_{MeOH}$=10:1, 15 mL×4). The combined organic phases were dried over anhydrous sodium sulfate and the dried solution was filtrated. The filtrate was concentrated and the residue was purified by Prep-TLC (MeOH:DCM) to give 7 (15 mg) with 56% yield.

MS-ESI calc. for $C_{33}H_{31}FN_3O_5S$ $[M+H]^+$600, found 600.

$^1H$ NMR (400 MHz, DMSO-$d_6$) δ 8.57 (d, J=8.8 Hz, 0.5H), 8.39 (d, J=8.8 Hz, 0.5H), 7.85-7.82 (m, 1H), 7.80 (d, J=8.0 Hz, 1H), 7.30-7.28 (m, 1H), 7.25-7.22 (m, 1H), 7.20-7.15 (m, 3H), 7.13-7.07 (m, 1H), 6.72 (d, J=4.0 Hz, 1H), 5.94-5.89 (m, 1H), 5.56-5.51 (m, 2H), 5.43-5.38 (m, 2H), 4.36-4.31 (m, 0.5H), 4.24-4.19 (m, 0.5H), 3.18-3.05 (m, 4H), 2.40 (s, 3H), 2.17-2.12 (m, 2H), 1.93-1.87 (m, 2H), 0.88-0.85 (m, 3H).

Example 8

8

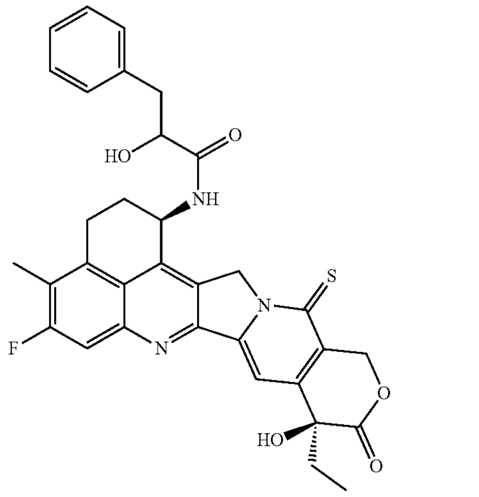

-continued

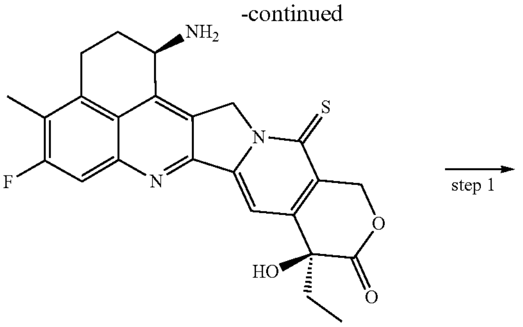

2-2

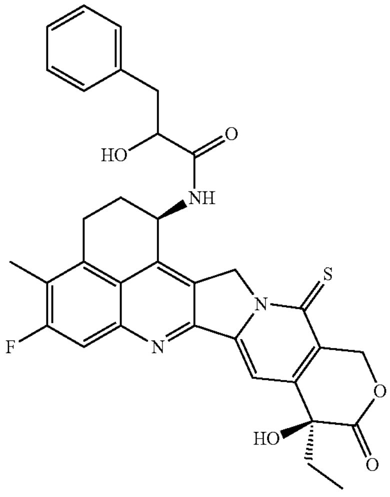

8

Step 1

To a round-bottom flask (25 mL) were added 2-2 (65 mg, 0.14 mmol), 2-hydroxy-3-phenylacetic acid (48 mg, 0.29 mmol) and anhydrous DCM (2 mL), N,N-diisopropylethylamine (55 mg, 0.43 mmol) and O-(7-azabenzotriazol-1-yl)-N,N,N',N'-tetramethyluroniumhexafluorophosphate (84 mg, 0.22 mmol) were then added, the resulting mixture was stirred at room temperature for 1.5 h. $H_2O$ (10 mL) was added to the reaction mixture. The aqueous phase was extracted with DCM/MeOH ($V_{DCM}$:$V_{MeOH}$=10:1, 150 mL×1). The organic phase was washed with brine (25 mL×2) and dried over anhydrous sodium sulfate. The dried solution was filtrated. The filtrate was concentrated and the residue was purified by Prep-TLC (MeOH:DCM) to give 8 (55 mg) with 64% yield.

MS-ESI calc. for $C_{33}H_{31}FN_3O_5S$ $[M+H]^+$600, found 600.

$^1H$ NMR (400 MHz, DMSO-$d_6$) δ 8.60 (d, J=9.2 Hz, 0.5H), 8.39 (d, J=8.8 Hz, 0.5H), 7.85-7.76 (m, 2H), 7.34-7.07 (m, 6H), 6.71 (s, 0.5H), 6.70 (s, 0.5H), 5.98-5.87 (m, 1H), 5.75-5.50 (m, 3H), 5.42-5.38 (m, 1H), 4.40-4.30 (m, 0.5H), 4.26-4.15 (m, 0.5H), 3.21-3.04 (m, 4H), 2.38 (s, 3H), 2.20-2.00 (m, 2H), 1.96-1.82 (m, 2H), 0.91-0.81 (m, 3H).

Example 9

9

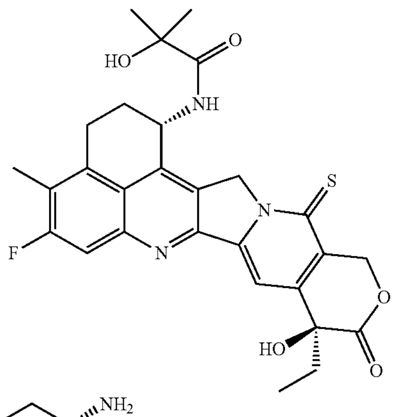

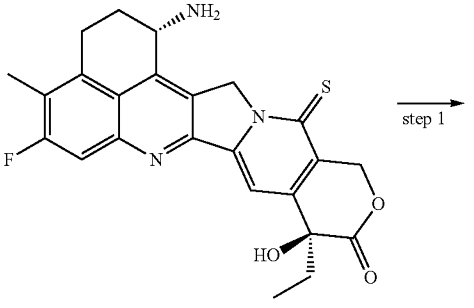

2-1

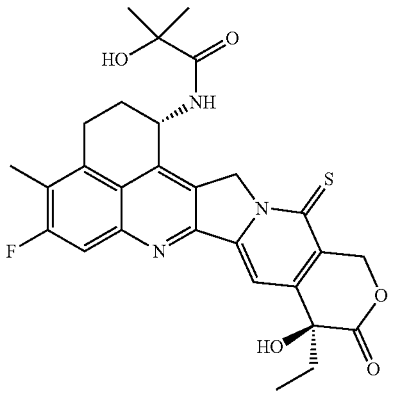

9

Step 1

To a round-bottom flask (25 mL) were added 2-1 (40 mg, 0.09 mmol), 2-hydroxyisobutyric acid (14 mg, 0.13 mmol) and anhydrous DCM (5 mL), N,N-diisopropylethylamine (29 mg, 0.22 mmol) and O-(7-azabenzotriazol-1-yl)-N,N,N',N'-tetramethyluroniumhexafluorophosphate (51 mg, 0.13 mmol) were then added, the resulting mixture was stirred at room temperature for 1 h. $H_2O$ (10 mL) was added to quench the reaction. The aqueous phase was extracted with DCM (20 mL×5). The combined organic phases were dried over anhydrous sodium sulfate and the dried solution was filtrated. The filtrate was concentrated and the residue was purified by Prep-TLC (MeOH:DCM) to give 9 (10 mg) with 21% yield.

MS-ESI calc. for $C_{28}H_{29}FN_3O_5S$ $[M+H]^+$538, found 538. $^1H$ NMR (400 MHz, DMSO-$d_6$) δ 8.45 (d, J=9.2 Hz, 1H), 7.82 (d, J=11.2 Hz, 1H), 7.79 (s, 1H), 6.71 (s, 1H), 5.90 (d, J=16.4 Hz, 1H), 5.62-5.50 (m, 4H), 5.36-5.28 (m, 1H), 3.32-3.20 (m, 1H), 3.18-3.04 (m, 1H), 2.39 (s, 3H), 2.24-2.13 (m, 2H), 1.93-1.79 (m, 2H), 1.53 (s, 3H), 1.37 (s, 3H), 0.90-0.81 (m, 3H).

Example 10

10

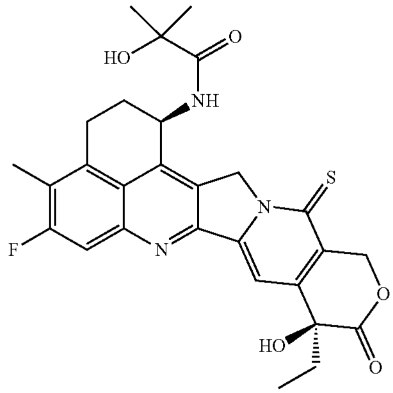

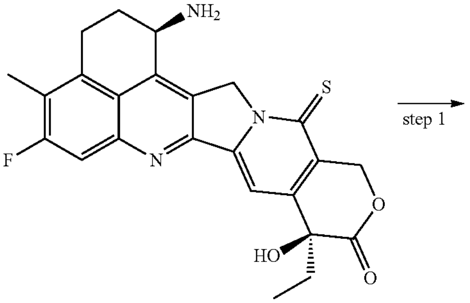

2-2

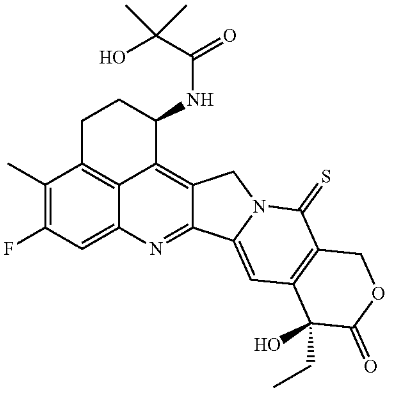

10

Step 1

To a round-bottom flask (25 mL) were added 2-2 (50 mg, 0.11 mmol), 2-hydroxyisobutyric acid (17 mg, 0.17 mmol) and anhydrous DCM (5 mL), N,N-diisopropylethylamine (36 mg, 0.28 mmol) and O-(7-azabenzotriazol-1-yl)-N,N,N',N'-tetramethyluroniumhexafluorophosphate (63 mg, 0.17 mmol) were then added, the resulting mixture was stirred at room temperature for 1 h. $H_2O$ (15 mL) was added to the reaction mixture. The aqueous phase was extracted with DCM (30 mL×3). The combined organic phases were dried over anhydrous sodium sulfate and the dried solution was filtrated. The filtrate was concentrated and the residue was purified by Prep-TLC (MeOH:DCM) to give 10 (30 mg) with 51% yield.

MS-ESI calc. for $C_{28}H_{29}FN_3O_5S$ $[M+H]^+$538, found 538.

$^1H$ NMR (400 MHz, DMSO-$d_6$) δ 8.46 (d, J=9.2 Hz, 1H), 7.83-7.74 (m, 2H), 6.71 (s, 1H), 5.91 (d, J=16.4 Hz, 1H), 5.64-5.44 (m, 4H), 5.24 (d, J=20.0 Hz, 1H), 3.29-3.18 (m, 1H), 3.17-3.08 (m, 1H), 2.37 (s, 3H), 2.22-2.09 (m, 2H), 1.96-1.85 (m, 2H), 1.55 (s, 3H), 1.37 (s, 3H), 0.87 (t, J=7.2 Hz, 3H).

Example 11

11

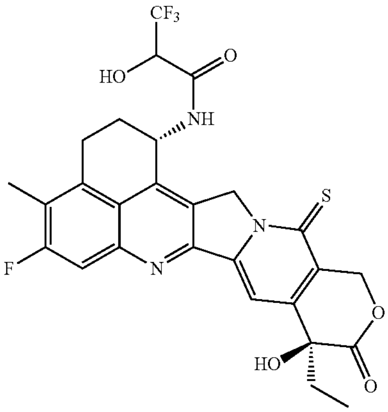

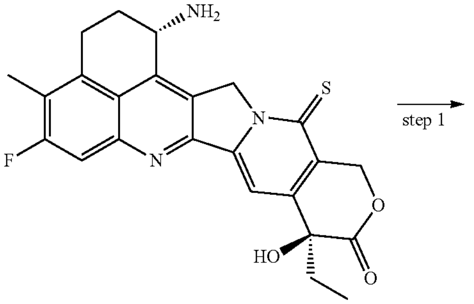

2-1

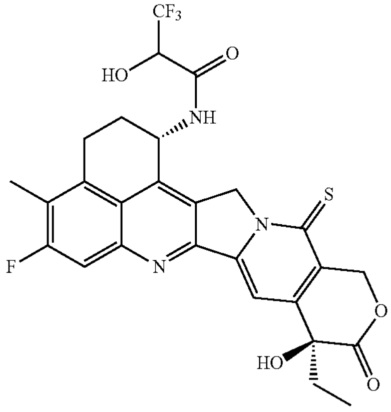

11

Step 1

To a round-bottom flask (25 mL) were added 2-1 (20 mg, 0.04 mmol), 3,3,3-trifluoro-2-methylpropanoic acid (13 mg, 0.09 mmol) and anhydrous N,N-dimethylformamide (2 mL), N,N-diisopropylethylamine (21 μL, 0.12 mmol) and O-(7- azabenzotriazol-1-yl)-N,N,N',N'-tetramethyluroniumhexafluorophosphate (23 mg, 0.06 mmol) were then added, the resulting mixture was stirred at room temperature for 1.5 h. $H_2O$ (30 mL) was added to the reaction mixture. The aqueous phase was extracted with DCM/MeOH ($V_{DCM}$:$V_{MeOH}$=10:1, 15 mL×4). The combined organic phases were dried over anhydrous sodium sulfate and the dried solution was filtrated. The filtrate was concentrated and the residue was purified by Prep-TLC (MeOH:DCM) to give 11-1 (2 mg) and 11-2 (5 mg) with 27% yield.

11-1 (Low Polarity):

MS-ESI calc. for $C_{27}H_{24}F_4N_3O_5S$ $[M+H]^+$578, found 578.

11-2 (High Polarity):

MS-ESI calc. for $C_{27}H_{24}F_4N_3O_5S$ $[M+H]^+$578, found 578.

Example 12

12

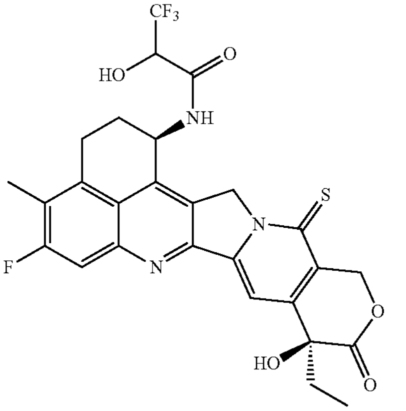

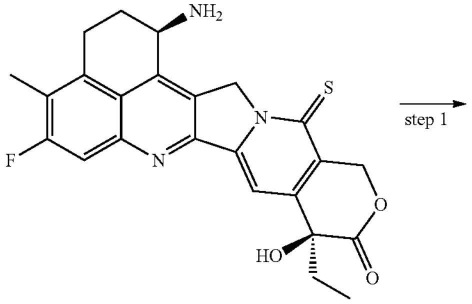

2-2

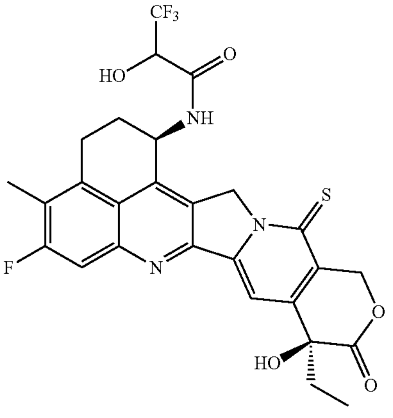

12

Step 1

To a round-bottom flask (25 mL) were added 2-2 (50 mg, 0.11 mmol), 3,3,3-trifluoro-2-methylpropanoic acid (23.9 mg, 0.17 mmol) and anhydrous DCM (4 mL), N,N-diisopropylethylamine (35.8 mg, 0.28 mmol) and O-(7-azabenzotriazol-1-yl)-N,N,N',N'-tetramethyluroniumhexafluorophosphate (75 mg, 0.19 mmol) were then added, the resulting mixture was stirred at room temperature for 4 h. $H_2O$ (15 mL) was added to the reaction mixture. The aqueous phase was extracted with DCM/MeOH ($V_{DCM}$:$V_{MeOH}$=10:1, 10 mL×6). The combined organic phases were dried over anhydrous sodium sulfate and the dried solution was filtrated. The filtrate was concentrated and the residue was purified by Prep-TLC (MeOH:DCM) to give 12-1 (15 mg) and 12-2 (6 mg) with 32% yield.

12-1 (Low Polarity):

MS-ESI calc. for $C_{27}H_{24}F_4N_3O_5S$ $[M+H]^+$578, found 578.

$^1$H NMR (400 MHz, DMSO-$d_6$) δ 9.01 (d, J=8.8 Hz, 1H), 7.83 (d, J=10.8 Hz, 1H), 7.81 (s, 1H), 7.36 (br s, 1H), 6.70 (br s, 1H), 5.92 (d, J=16.4 Hz, 1H), 5.67-5.59 (m, 2H), 5.52 (d, J=16.4 Hz, 1H), 5.41 (s, 2H), 4.73-4.61 (m, 1H), 3.18 (t, J=6.4 Hz, 2H), 2.40 (s, 3H), 2.31-2.21 (m, 1H), 2.20-2.10 (m, 1H), 1.96-1.84 (m, 2H), 0.87 (t, J=7.2 Hz, 3H).

12-2 (High Polarity):

MS-ESI calc. for $C_{27}H_{24}F_4N_3O_5S$ $[M+H]^+$578, found 578.

$^1$H NMR (400 MHz, DMSO-$d_6$) δ 8.97 (d, J=8.4 Hz, 1H), 7.85 (d, J=10.8 Hz, 1H), 7.80 (s, 1H), 7.17-7.09 (m, 1H), 6.72 (br s, 1H), 5.91 (d, J=16.4 Hz, 1H), 5.68-5.59 (m, 1H), 5.58-5.33 (m, 3H), 4.66-4.55 (m, 1H), 3.20-3.12 (m, 2H), 2.40 (s, 3H), 2.28-2.09 (m, 2H), 1.93-1.83 (m, 2H), 0.86 (t, J=7.2 Hz, 3H).

Example 13

13

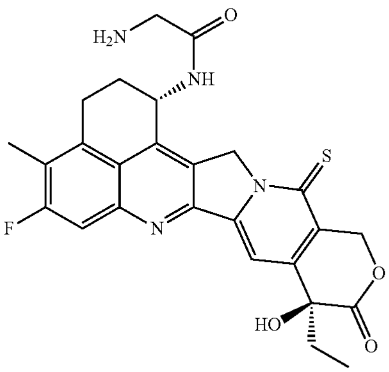

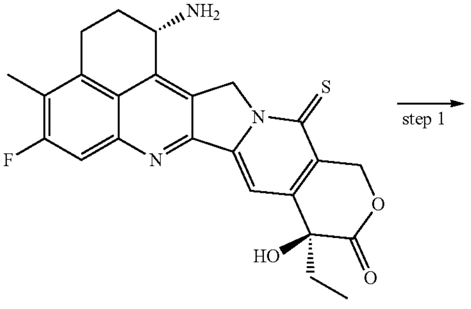

2-1

-continued

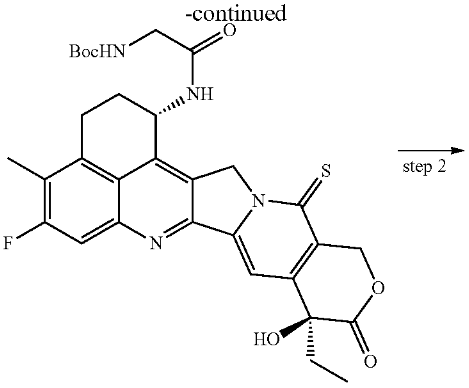

13a

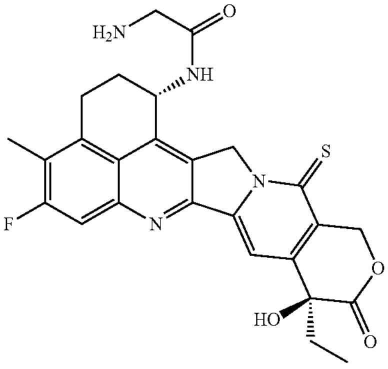

13

Step 1

To a round-bottom flask (25 mL) were added 2-1 (20 mg, 0.04 mmol), Boc-glycine (16 mg, 0.09 mmol) and anhydrous N,N-dimethylformamide (2 mL), N,N-diisopropylethylamine (21 μL, 0.12 mmol) and O-(7-azabenzotriazol-1-yl)-N,N,N',N'-tetramethyluroniumhexafluorophosphate (23 mg, 0.06 mmol) were then added, the resulting mixture was stirred at room temperature for 1.5 h. $H_2O$ (40 mL) was added to the reaction mixture. The aqueous layer was extracted with DCM/MeOH ($V_{DCM}$:$V_{MeOH}$=10:1, 15 mL×4). The combined organic phases were dried over anhydrous sodium sulfate and the dried solution was filtrated. The filtrate was concentrated and the residue was purified by Prep-TLC (MeOH:DCM) to give 13a (15 mg) with 56% yield.

MS-ESI calc. for $C_{31}H_{34}FN_4O_6S$ $[M+H]^+$609, found 609.

Step 2

Hydrogen chloride (ethyl acetate solution, 4.0 M, 2 mL) was added dropwise to a solution of 13a (15 mg, 0.02 mmol) in ethyl acetate (2 mL) in a round-bottom flask (25 mL), the resulting mixture was stirred at room temperature for 7 h. Another batch of hydrogen chloride (1,4-dioxane solution, 4.0 M, 1 mL) was added and the mixture was stirred for additional 1 h. The reaction mixture was added slowly to a cold saturated aqueous sodium bicarbonate (50 mL) until no bubbles generated. The aqueous phase was extracted with DCM/MeOH ($V_{DCM}V_{MeOH}$=10:1, 30 mL×6). The combined organic phases were dried over anhydrous sodium sulfate and the dried solution was filtrated. The filtrate was concentrated and the residue was purified by Prep-HPLC to give 13 (2 mg) with 15% yield.

MS-ESI calc. for $C_{26}H_{26}FN_4O_4S$ $[M+H]^+$509, found 509.

Example 14

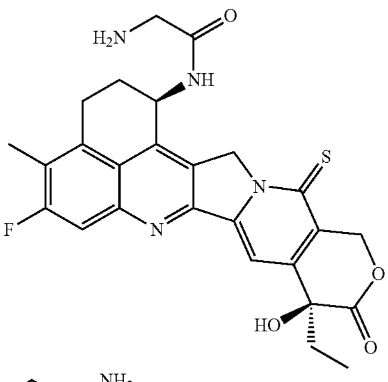

14

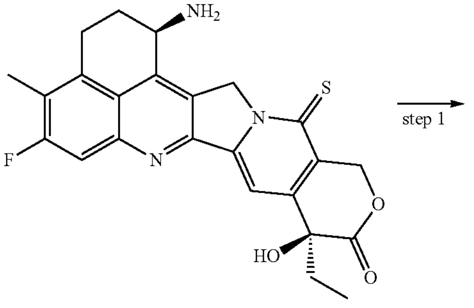

2-2

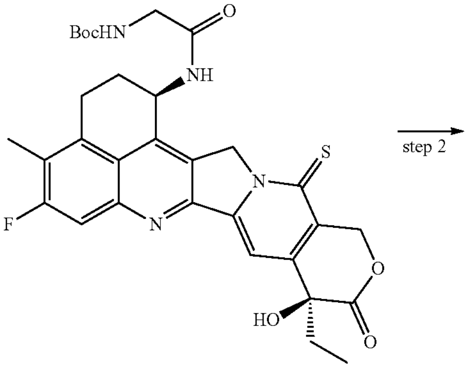

14a

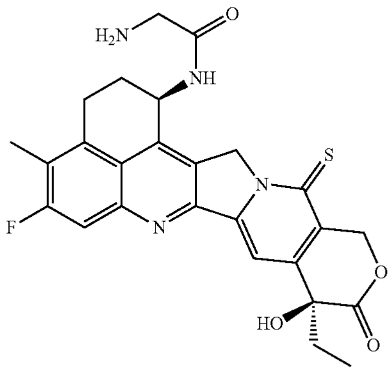

14

Step 1

To a round-bottom flask (25 mL) were added 2-2 (100 mg, 0.22 mmol), Boc-glycine (77 mg, 0.44 mmol) and anhydrous DCM (4 mL), N,N-diisopropylethylamine (85 mg, 0.66 mmol) and O-(7-azabenzotriazol-1-yl)-N,N,N',N'-tetramethyluroniumhexafluorophosphate (100 mg, 0.26 mmol) were then added, the resulting mixture was stirred at room temperature for 1 h. $H_2O$ (10 mL) was added to the reaction mixture. The aqueous phase was extracted with DCM/MeOH ($V_{DCM}$:$V_{MeOH}$=10:1, 150 mL×1). The organic phase was washed with brine (25 mL×2) and dried over anhydrous sodium sulfate. The dried solution was filtrated. The filtrate was concentrated to give crude product 14a (140 mg).

MS-ESI calc. for $C_{31}H_{34}FN_4O_6S$ $[M+H]^+$609, found 609.

Step 2

Hydrogen chloride (ethyl acetate solution, 4.0 M, 4 mL) was added dropwise to a solution of 14a (125 mg) in ethyl acetate (4 mL), the resulting mixture was stirred at room temperature for 17 h. The reaction mixture was added slowly to a cold saturated aqueous sodium bicarbonate to adjust the pH to 8-9. The aqueous phase was extracted with DCM/MeOH ($V_{DCM}$:$V_{MeOH}$=10:1, 200 mL×3). The combined organic phases were dried over anhydrous sodium sulfate and the dried solution was filtrated. The filtrate was concentrated and the residue was trituratedin acetonitrile (2 mL) to give 14 (60 mg) with 54% yield.

MS-ESI calc. for $C_{26}H_{26}FN_4O_4S$ $[M+H]^+$509, found 509.

$^1H$ NMR (400 MHz, DMSO-$d_6$) δ 8.60 (br s, 1H), 7.82 (d, J=10.8 Hz, 1H), 7.79 (s, 1H), 6.71 (br s, 1H), 5.90 (d, J=16.8 Hz, 1H), 5.66-5.58 (m, 1H), 5.56-5.45 (m, 2H), 5.41-5.37 (m, 1H), 3.30-3.10 (m, 4H), 2.38 (s, 3H), 2.24-2.14 (m, 2H), 1.96-1.82 (m, 2H), 0.86 (t, J=7.2 Hz, 3H).

Example 15

15

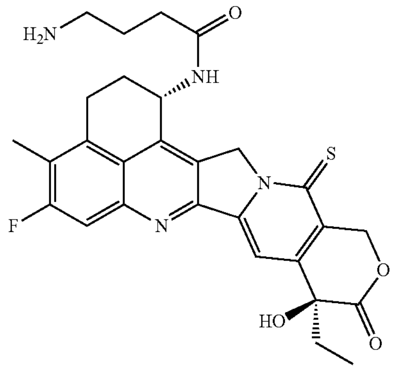

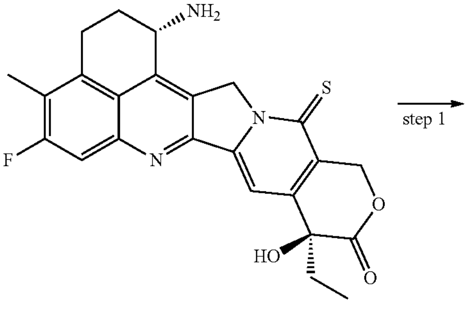

2-1

-continued

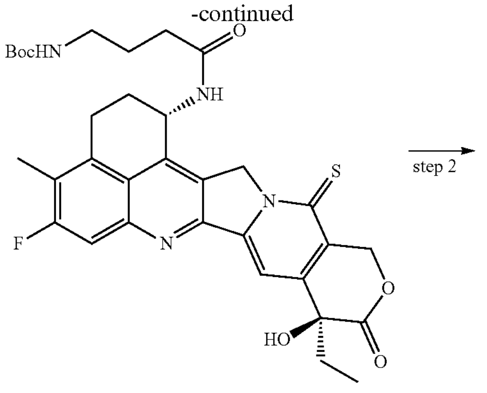

15a

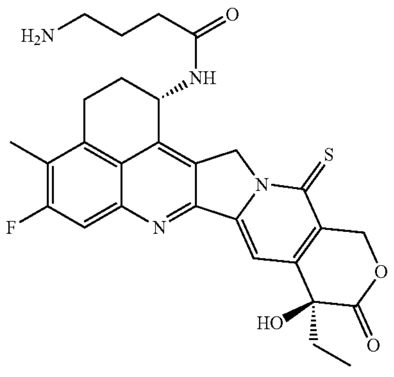

15

Step 1

To a round-bottom flask (25 mL) were added 2-1 (30 mg, 0.07 mmol), Boc-GABA-OH (28 mg, 0.14 mmol) and anhydrous N,N-dimethylformamide (3 mL), N,N-diisopropylethylamine (37 μL, 0.21 mmol) and O-(7-azabenzotriazol-1-yl)-N,N,N',N'-tetramethyluroniumhexafluorophosphate (40 mg, 0.11 mmol) were then added, the resulting mixture was stirred at room temperature for 1.5 h. $H_2O$ (50 mL) was added to the reaction mixture. The aqueous phase was extracted with DCM/MeOH ($V_{DCM}$:$V_{MeOH}$=10:1, 15 mL×4). The combined organic phases were dried over anhydrous sodium sulfate. The dried solution was filtrated. The filtrate was concentrated and the residue was purified by Prep-TLC (MeOH:DCM) to give 15a (17 mg) with 40% yield.

MS-ESIcalc. For $C_{33}H_{38}FN_4O_6S$ $[M+H]^+$637, found 637.

Step 2

Hydrogen chloride (1,4-dioxane solution, 4.0 M, 4 mL) was added dropwise to a solution of 15a (17 mg, 0.03 mmol) in 1,4-dioxane (1 mL) in a round-bottom flask (25 mL), the resulting mixture was stirred at room temperature for 1 h. The reaction mixture was added slowly to a cold saturated aqueous sodium bicarbonate solution (60 mL) until no bubbles generated. The aqueous phase was extracted with DCM/MeOH ($V_{DCM}$:$V_{MeOH}$=10:1, 30 mL×6). The combined organic phases were dried over anhydrous sodium sulfate and the dried solution was filtrated. The filtrate was concentrated and the residue was purified by Prep-HPLC to give 15 (3 mg) with 21% yield.

MS-ESI calc. For $C_{28}H_{30}FN_4O_4S$ $[M+H]^+$537, found 537.

$^1$H NMR (400 MHz, DMSO-$d_6$) δ 8.67 (d, J=8.8 Hz, 1H), 8.37 (s, 1H), 7.85 (d, J=10.8 Hz, 1H), 7.80 (s, 1H), 6.73 (br s, 1H), 5.91 (d, J=16.8 Hz, 1H), 5.64-5.59 (m, 1H), 5.53-5.45 (m, 3H), 3.25-3.10 (m, 2H), 2.79-2.75 (m, 2H), 2.41 (s, 3H), 2.35-2.32 (m, 2H), 2.24-2.11 (m, 2H), 1.92-1.80 (m, 4H), 0.85 (t, J=7.2 Hz, 3H).

Example 16

16

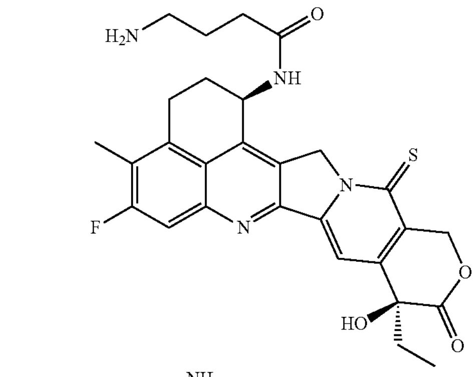

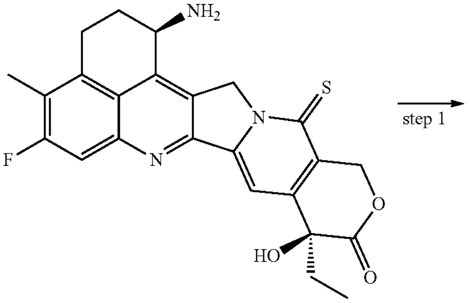

2-2

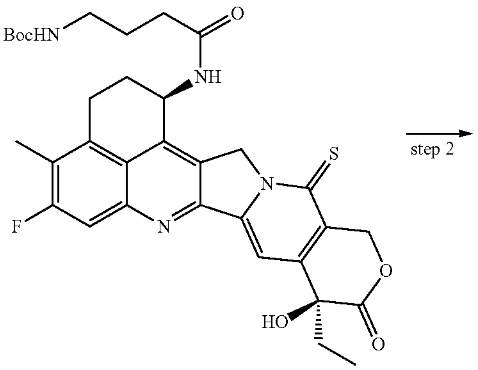

16a

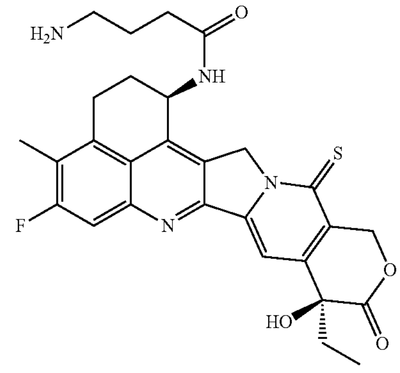

16

Step 1

To a round-bottom flask (25 mL) were added 2-2 (100 mg, 0.22 mmol), Boc-GABA-OH (90 mg, 0.44 mmol) and anhydrous DCM (5 mL), N,N-diisopropylethylamine (86 mg, 0.66 mmol) and O-(7-azabenzotriazol-1-yl)-N,N,N',N'-tetramethyluroniumhexafluorophosphate (121 mg, 0.32 mmol) were then added, the resulting mixture was stirred at room temperature for 4 h. $H_2O$ (30 mL) was added to the reaction mixture. The aqueous phase was extracted with DCM/MeOH ($V_{DCM}$:$V_{MeOH}$=10:1, 50 mL×4). The combined organic phases were dried over anhydrous sodium sulfate. The dried solution was filtrated. The filtrate was concentrated and the residue was purified by flash column chromatography on silica gel (MeOH:DCM=0-100%) to give 16a (106 mg) with 75% yield.

MS-ESI calc. For $C_{33}H_{38}FN_4O_6S$ $[M+H]^+$637, found 637.

Step 2

Hydrogen chloride (ethyl acetate solution, 4.0 M, 5 mL) was added dropwise to a solution of 16a (106 mg, 0.17 mmol) in ethyl acetate (5 mL) in a round-bottom flask (25 mL), the resulting mixture was stirred at room temperature for 17 h. The reaction mixture was added slowly to a cold saturated aqueous sodium bicarbonate. The aqueous phase was extracted with DCM/MeOH ($V_{DCM}$:$V_{MeOH}$=10:1, 50 mL×4). The combined organic phases were dried over anhydrous sodium sulfate and the dried solution was filtrated. The filtrate was concentrated and the residue was purified by Prep-HPLC to give 16 (4 mg) with 4% yield.

MS-ESI calc. For $C_{28}H_{30}FN_4O_4S$ $[M+H]^+$537, found 537.

$^1$H NMR (400 MHz, DMSO-$d_6$) δ 8.73 (d, J=8.8 Hz, 1H), 8.39 (br s, 1H), 7.83 (d, J=10.8 Hz, 1H), 7.80 (s, 1H), 5.91 (d, J=16.4 Hz, 1H), 5.64-5.56 (m, 1H), 5.55-5.34 (m, 3H), 3.19-3.10 (m, 2H), 2.80 (t, J=7.6 Hz, 2H), 2.39 (s, 3H), 2.35 (t, J=7.2 Hz, 2H), 2.25-2.05 (m, 2H), 2.04-1.93 (m, 1H), 1.94-1.80 (m, 3H), 0.86 (t, J=7.2 Hz, 3H).

Example 17

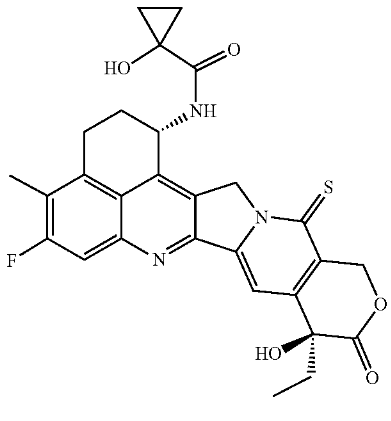

17

-continued

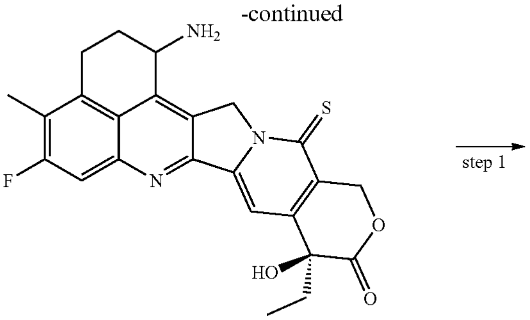

1f

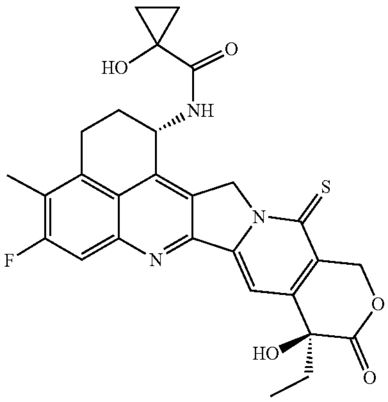

17

Step 1

To a round-bottom flask (25 mL) were added if (100 mg, 0.22 mmol), 1-hydroxy-1-cyclopropanecarboxylic acid (45 mg, 0.44 mmol) and anhydrous DCM (3 mL), N,N-diisopropylethylamine (85 mg, 0.66 mmol) and O-(7-azabenzotriazol-1-yl)-N,N,N',N'-tetramethyluroniumhexafluorophosphate (108 mg, 0.29 mmol) were then added, the resulting mixture was stirred at room temperature for 3 h. $H_2O$ (15 mL) was added to the reaction mixture. The aqueous layer was extracted with DCM (150 mL×1). The organic phase was washed with brine (15 mL×2) and dried over anhydrous sodium sulfate. The dried solution was filtrated. The filtrate was concentrated and the residue was purified by Prep-HPLC to give 17 (12 mg) with 10% yield.

MS-ESI calc. for $C_{28}H_{27}FN_3O_5S$ $[M+H]^+$536, found 536.

$^1$H NMR (400 MHz, DMSO-$d_6$) δ 8.62 (d, J=8.8 Hz, 1H), 7.84-7.79 (m, 1H), 7.79 (s, 1H), 6.70 (s, 1H), 6.27 (s, 1H), 5.91 (d, J=16.8 Hz, 1H), 5.66-5.57 (m, 1H), 5.56-5.46 (m, 2H), 5.35-5.24 (m, 1H), 3.32-3.21 (m, 1H), 3.20-3.05 (m, 1H), 2.39 (s, 3H), 2.35-2.15 (m, 2H), 1.38-1.15 (m, 2H), 1.04-0.90 (m, 2H), 0.85 (t, J=7.2 Hz, 3H).

Example 18

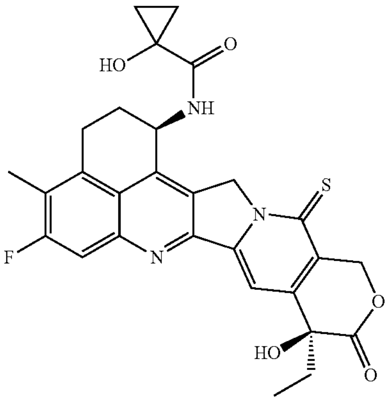

18

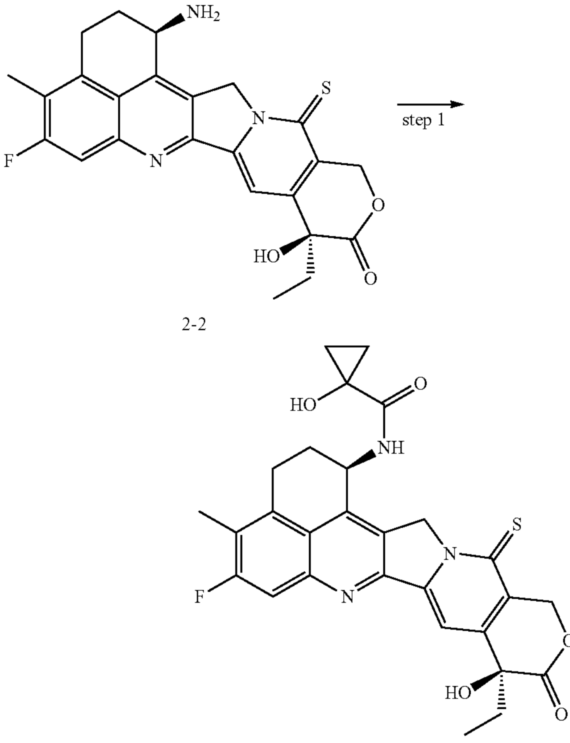

2-2

18

Step 1

To a round-bottom flask (25 mL) were added 2-2 (70 mg, 0.16 mmol), 1-hydroxy-1-cyclopropanecarboxylic acid (33 mg, 0.32 mmol) and anhydrous N,N-dimethylformamide (2 mL), N,N-diisopropylethylamine (60 mg, 0.47 mmol) and O-(7-azabenzotriazol-1-yl)-N, N,N,N'-tetramethyluroniumhexafluorophosphate (91 mg, 0.24 mmol) were then added, the resulting mixture was stirred at room temperature for 3 h. $H_2O$ (15 mL) was added to the reaction mixture. The aqueous phase was extracted with ethyl acetate (150 mL×1). The organic phase was washed with brine (25 mL×5) and dried over anhydrous sodium sulfate. The dried solution was filtrated. The filtrate was concentrated and the residue was purified by Prep-TLC (MeOH:DCM) to give 18 (28 mg) with 34% yield.

MS-ESI calc. for $C_{28}H_{27}FN_3O_5S$ $[M+H]^+$536, found 536. $^1H$ NMR (400 MHz, DMSO-$d_6$) δ 8.65 (d, J=9.2 Hz, 1H), 7.81 (d, J=11.2 Hz, 1H), 7.79 (s, 1H), 6.70 (s, 1H), 6.29 (s, 1H), 5.92 (d, J=16.8 Hz, 1H), 5.66-5.58 (m, 1H), 5.56-5.46 (m, 2H), 5.92 (d, J=20.0 Hz, 1H), 3.32-3.20 (m, 1H), 3.20-3.05 (m, 1H), 2.39 (s, 3H), 1.95-1.84 (m, 2H), 1.38-1.16 (m, 2H), 1.05-0.90 (m, 2H), 0.86 (t, J=7.2 Hz, 3H).

Example 19

19

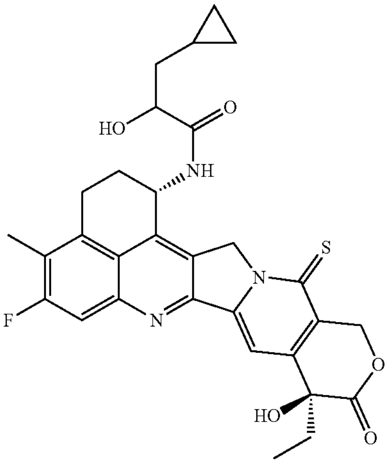

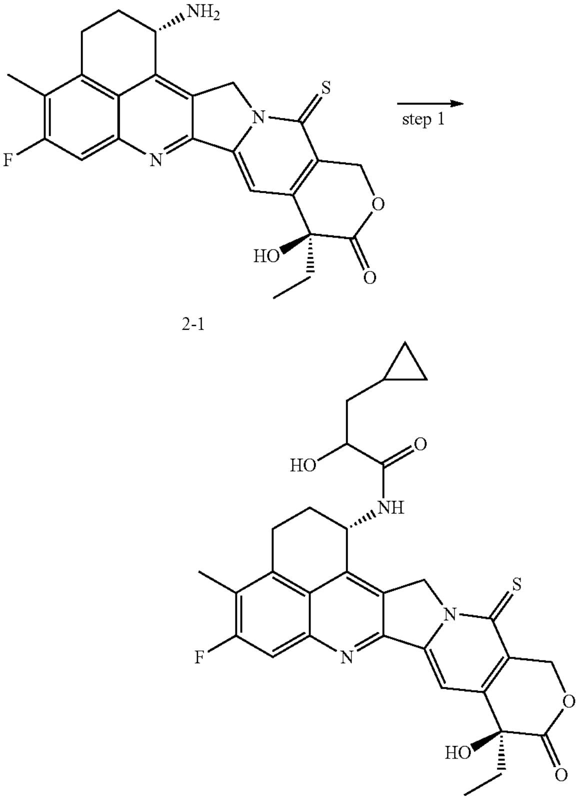

2-1

19

Step 1

To a round-bottom flask (25 mL) were added 2-1 (30 mg, 0.07 mmol), 3-cyclopropyl-2-hydroxypropanoic acid (22 mg, 0.17 mmol) and anhydrous DCM (3 mL), N,N-diisopropylethylamine (23 mg, 0.18 mmol) and O-(7-azabenzotriazol-1-yl)-N,N,N',N'-tetramethyluroniumhexafluorophosphate (42 mg, 0.11 mmol) were then added, the resulting mixture was stirred at room temperature for 1 h. The reaction mixture was concentrated and the residue was purified by Prep-TLC (MeOH:DCM) to give 19 (6 mg) with 16% yield.

MS-ESI calc. for $C_{30}H_{31}FN_3O_5S$ $[M+H]^+$564, for 564.

$^1H$ NMR (400 MHz, DMSO-$d_6$) δ 8.50 (d, J=8.8 Hz, 1H), 7.81 (d, J=10.8 Hz, 1H), 7.79 (s, 1H), 6.71 (s, 1H), 5.90 (d, J=16.4 Hz, 1H), 5.63-5.55 (m, 1H), 5.62-5.46 (m, 3H), 5.35 (d, J=20.0 Hz, 1H), 4.27-4.05 (m, 1H), 3.29-3.20 (m, 1H), 3.19-3.05 (m, 1H), 2.40 (s, 3H), 2.29-2.08 (m, 2H), 1.74-1.63 (m, 2H), 1.72-1.62 (m, 1H), 1.62-1.49 (m, 1H), 0.97-0.89 (m, 1H), 0.85 (t, J=7.4 Hz, 3H), 0.50-0.28 (m, 2H), 0.20-0.02 (m, 2H).

Example 20

20

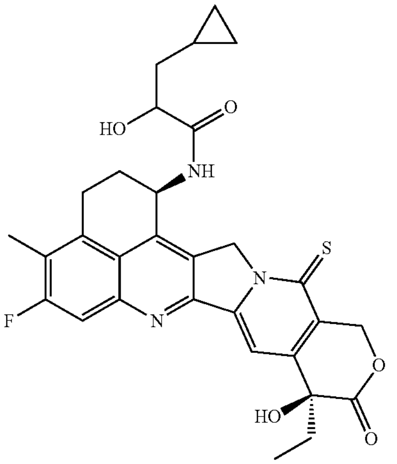

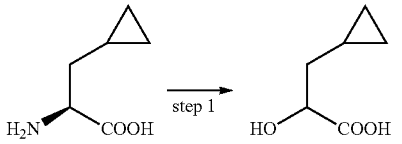

20a 20b

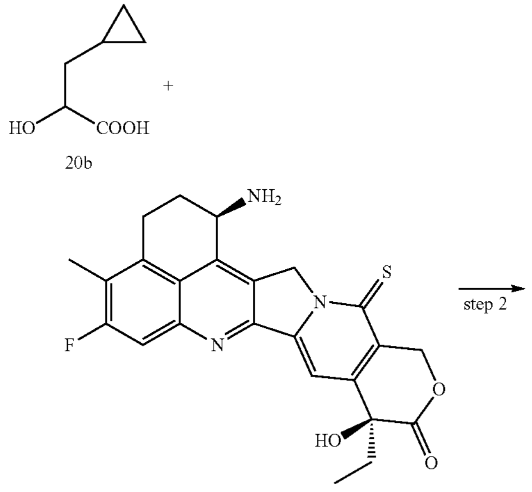

20b 2-2

-continued

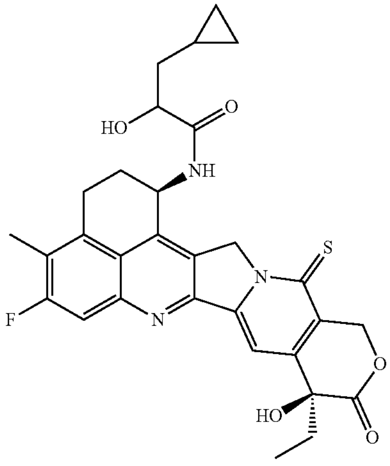

20

Step 1

20a (500 mg, 3.87 mmol), $H_2O$ (4 mL) and acetic acid (930 mg, 15.48 mmol) were added to a round-bottom flask (25 mL), the reaction mixture was cooled down to 0-5° C. followed by addition of a solution of $NaNO_2$ in water (2 mL, 7.7 mmol/mL), after the addition, the mixture was warmed to room temperature and continued to stir for 3 h. The aqueous phase was extracted with ethyl acetate (20 mL×5). The combined organic phases were dried over anhydrous sodium sulfate. The dried solution was filtrated and the filtrate was concentrated to give crude product 20b (200 mg).

Step 2

To a round-bottom flask (25 mL) were added 2-2 (30 mg, 0.07 mmol), 20b (90 mg, 0.69 mmol) and anhydrous DCM (5 mL), N,N-diisopropylethylamine (15.2 mg, 0.28 mmol) and O-(7-azabenzotriazol-1-yl)-N,N,N',N'-tetramethyluroniumhexafluorophosphate (34 mg, 0.09 mmol) were then added, the resulting mixture was stirred at room temperature for 1 h. $H_2O$ (10 mL) was added to the reaction mixture. The aqueous phase was extracted with DCM (30 mL×3). The combined organic phases were dried over anhydrous sodium sulfate. The dried solution was filtrated. The filtrate was concentrated and the residue was purified by Prep-TLC (MeOH:DCM) to give 20 (5 mg) with 13% yield.

MS-ESI calc. for $C_{30}H_{31}FN_3O_5S$ $[M+H]^+$564, found 564.

$^1H$ NMR (400 MHz, DMSO-$d_6$) δ 8.51 (d, J=8.8 Hz, 1H), 7.78-7.65 (m, 2H), 6.69 (s, 1H), 5.86 (d, J=16.4 Hz, 1H), 5.66 (d, J=5.6 Hz, 1H), 5.60-5.34 (m, 3H), 5.20 (d, J=20.0 Hz, 1H), 4.10-3.91 (m, 1H), 3.25-3.13 (m, 1H), 3.13-2.99 (m, 1H), 2.31 (s, 3H), 2.12 (q, J=6.8 Hz, 2H), 1.99-1.75 (m, 3H), 1.63-1.42 (m, 1H), 0.95-0.86 (m, 1H), 0.83 (t, J=7.3 Hz, 3H), 0.50-0.26 (m, 2H), 0.19-0.07 (m, 2H).

Example 21

21

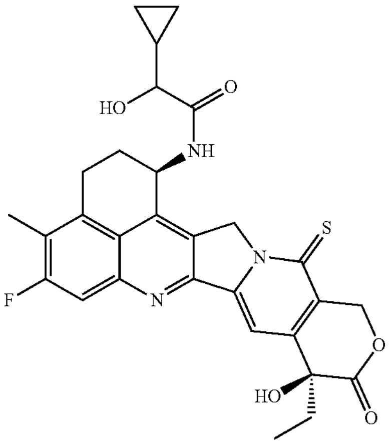

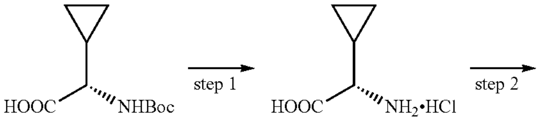

21a 21b

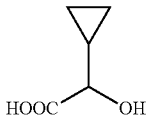

21c

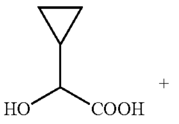

21c

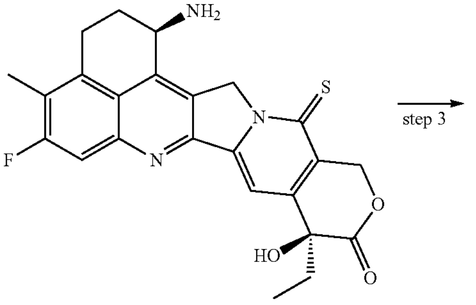

2-2

-continued

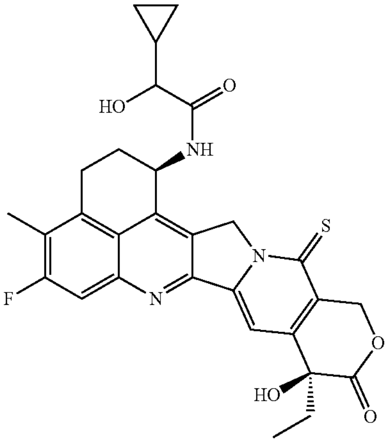

21

Step 1

Hydrogen chloride (ethyl acetate solution, 4.0 M, 7.4 mL) was added dropwise to a solution of 21a (800 mg, 3.72 mmol) in ethyl acetate (4 mL) in a round-bottom flask (25 mL), the resulting mixture was stirred at room temperature for 17 h. The reaction mixture was filtrated. The filter cake was flushed with ethyl acetate (5 mL). The collected solid was dried to give 21b (570 mg) with 99% yield.

$^1$H NMR (400 MHz, DMSO-$d_6$) δ 13.63 (br s, 1H), 8.52 (s, 3H), 3.22 (d, J=8.8 Hz, 1H), 1.16-1.02 (m, 1H), 0.68-0.50 (m, 4H).

Step 2

21b (330 mg, 2.20 mmol) was dissolved in sulfuric acid (2.0 N, 4.4 mL), the reaction mixture was cooled down to 0-5° C. followed by addition of a solution of $NaNO_2$ in water (5 mL, 4.4 mmol/mL), after the addition, the resulting mixture was slowly warmed to room temperature and continued to stir overnight. Sodium chloride was added to the reaction mixture until it is saturated. The aqueous phase was extracted with ethyl acetate (100 mL×3). The combined organic phases were dried over anhydrous sodium sulfate. The dried solution was filtrated and the filtrate was concentrated to give crude product 21c (150 mg).

Step 3

To a round-bottom flask (25 mL) were added 2-2 (100 mg, 0.22 mmol), 21c (130 mg) and anhydrous DCM (5 mL), N,N-diisopropylethylamine (113 mg, 0.88 mmol) and O-(7-azabenzotriazol-1-yl)-N,N,N',N'-tetramethyluroniumhexafluorophosphate (125 mg, 0.33 mmol) were then added, the resulting mixture was stirred at room temperature for 2 h. DCM/MeOH ($V_{DCM}$:$V_{MeOH}$=10:1, 200 mL) was added to the reaction mixture, the organic phase was washed with $HCl_{(aq)}$ (1.0 N, 20 mL×1), brine (25 mL×2) and dried over anhydrous sodium sulfate. The dried solution was filtrated. The filtrate was concentrated and the residue was purified by Prep-TLC (MeOH:DCM) to give 21 (5 mg) with 4% yield.

MS-ESI calc. for $C_{29}H_{29}FN_3O_5S$ $[M+H]^+$550, found 550.

$^1$H NMR (400 MHz, DMSO-$d_6$) δ 8.75 (d, J=8.8 Hz, 1H), 7.85 (d, J=10.4 Hz, 1H), 7.80 (S, 1H), 6.69 (s, 1H), 5.92 (d, J=16.4 Hz, 1H), 5.64-5.56 (m, 1H), 5.56-5.46 (m, 2H), 5.43-5.34 (m, 1H), 4.66-4.60 (m, 1H), 3.48-3.30 (m, 1H), 3.22-3.12 (m, 1H), 2.41 (s, 3H), 2.26-2.10 (m, 2H), 1.94-1.82 (m, 2H), 1.11-1.05 (m, 1H), 0.90-0.72 (m, 7H).

Biological Activity Test

Cell Proliferation Inhibition Test KPL-4 Cells in the logarithmic phase of growth were collected and re-suspended with fresh RPMI1640 complete cell culture medium, and adjusted to $2\times10^4$ cells/mL after cell counting. Cells were seeded into 96-well cell culture plates at 100 μL/well, and placed in a $CO_2$ incubator (37° C., 5% $CO_2$) overnight. In the next day, one of the cell culture plates were taken out, balanced to room temperature, and CellTiter-Glo reagent (Promega, USA), which was pre-balanced to room temperature and evenly mixed, was added into the plate at 100 μl. The plate was kept in dark for 30 min, and then luminescence value was read with a microplate reader (denoted as $G_0$ value). The other cell culture plates were taken out and added with different concentrations of test compounds or DMSO (final concentration 0.5%) in corresponding wells. After incubated for 72 h in a $CO_2$ incubator, the cell culture plates were balanced to room temperature and tested for cell viabilities using CellTiter-Glo reagent as described above (denoted as $G_3$ value).

The cell proliferation rates were calculated using the following formula: Cell proliferation rate (%)=(mean of $G_{3compound}$−mean of $G_0$)/(mean of $G_{3DMSO}$−mean of $G_0$)×100. Inhibition curves were fitted with GraphPad Prism and $GI_{50}$ values were obtained (shown in the table below).

| Example | $GI_{50}$ (nM) |
|---|---|
| Example 1: 1-1 | 13.9 |
| Example 1: 1-2 | 10.3 |
| Example 2: 2-1 | <1.52 |
| Example 2: 2-2 | 2.47 |
| Example 3 | 2.59 |
| Example 4 | 1.55 |
| Example 5 | 1.79 |
| Example 6 | 5.31 |
| Example 7 | 5.76 |
| Example 8 | 4.95 |
| Example 9 | 12.1 |
| Example 10 | 3.54 |
| Example 11: 11-1 | 17.3 |
| Example 11: 11-2 | 23.5 |
| Example 12: 12-1 | 5.8 |
| Example 12: 12-2 | 6.4 |
| Example 13 | 7.54 |
| Example 14 | 6.14 |
| Example 17 | 1.83 |
| Example 18 | 3.89 |
| Example 19 | 2.9 |
| Example 20 | 4.79 |
| Example 21 | 34.7 |
| DXd | 72 |

The results indicated that, the compounds of the invention showed high inhibitory activities against proliferation of the tumor cells, with higher potency than DXd (derivative of Exatecan, structure shown below). Because the compounds of the invention have excellent inhibitory activity against tumor cell proliferation, they can be used as oncology drugs, or as toxins for the preparation of antibody-drug conjugates for the treatment of tumors.

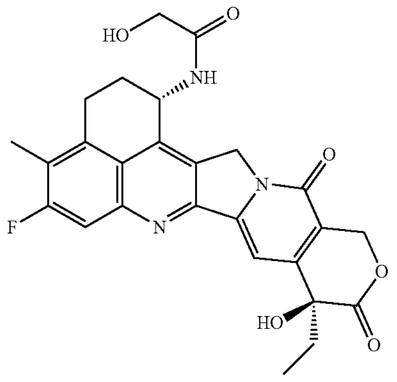

DXd
(derivative of Exatecan)

All documents referred to in the present invention are incorporated by reference herein as if each document is individually incorporated by reference. Further, it should be understood that upon reading the above teaching of the present invention, various modifications or modifications may be made to the present invention by those skilled in the art, and those equivalents also fall within the scope defined by the appended claims of the present application.

The invention claimed is:

1. A compound of formula (I), or a pharmaceutically acceptable salt thereof:

(I)

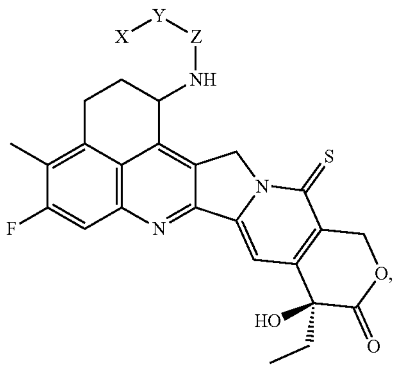

wherein:

X is selected from the group consisting of H, OH, and $NH_2$;

Y is $(CR^1R^2)_n$;

Z is chemical bond or C(O);

n is selected from 0, 1, 2, or 3;

and when n is 2 or 3, each $CR^1R^2$ is the same or different;

$R^1$ and $R^2$ are independently selected from the group consisting of hydrogen, deuterium, halogen, $C_1$-$C_8$ alkyl, $C_1$-$C_8$ haloalkyl, $C_1$-$C_8$ deuterated alkyl, $C_1$-$C_8$ hydroxyalkyl, and $C_3$-$C_8$ cycloalkyl;

or, $R^1$ and $R^2$ together with their attached carbon atoms form a $C_3$-$C_8$ cycloalkyl;

and $C_1$-$C_8$ alkyl is optionally substituted by substituents selected from the group consisting of $C_6$-$C_{10}$ aryl, $C_3$-$C_6$ cycloalkyl.

2. The compound according to claim 1, or a pharmaceutically acceptable salt thereof, wherein the compound has a structure as shown in the following formula:

-continued
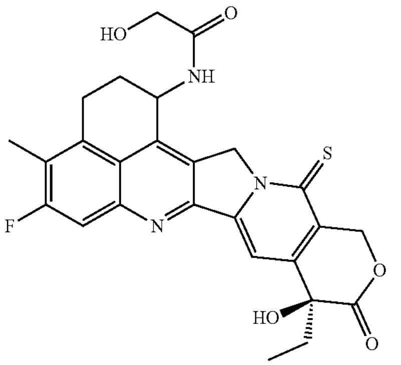
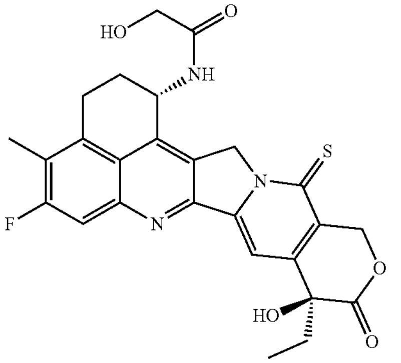
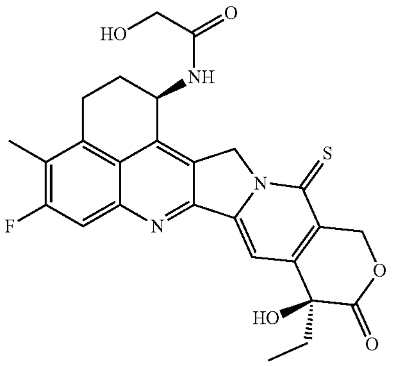
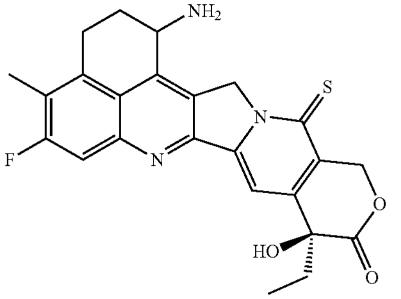
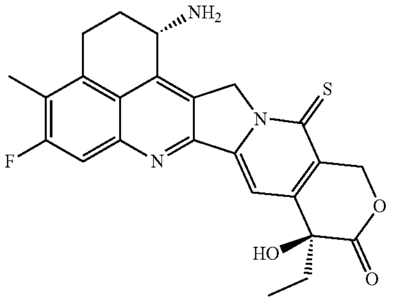
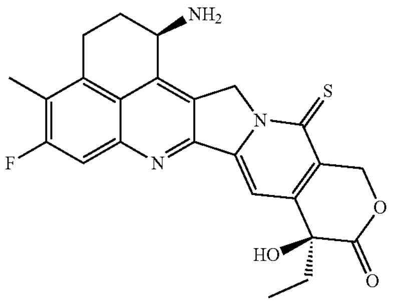
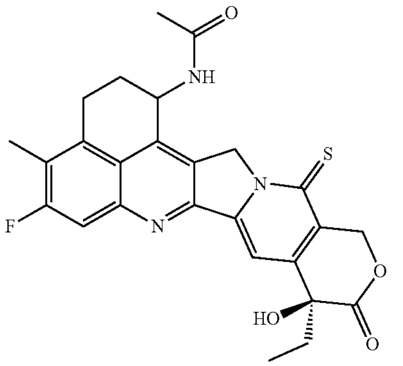
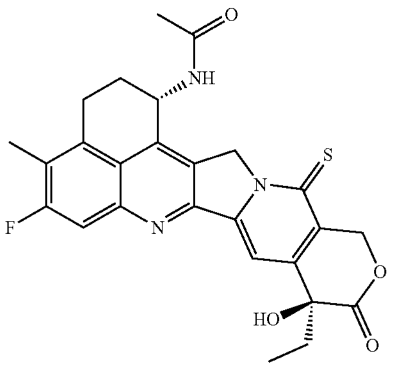
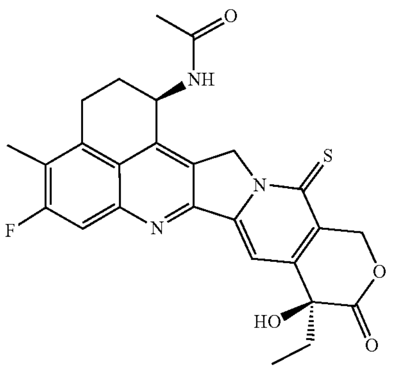

-continued
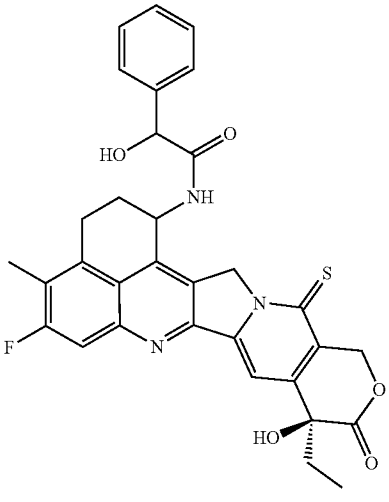
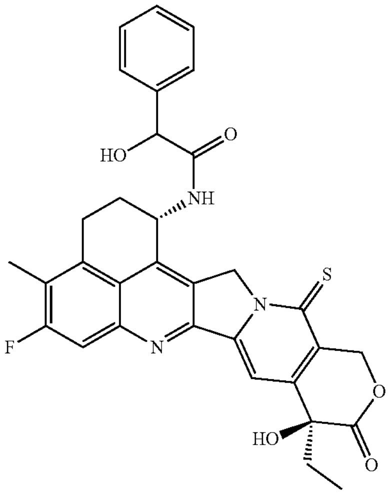
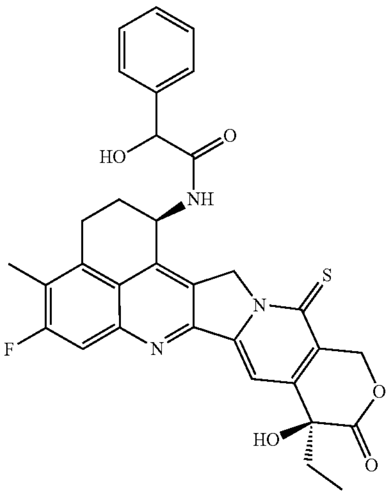
-continued
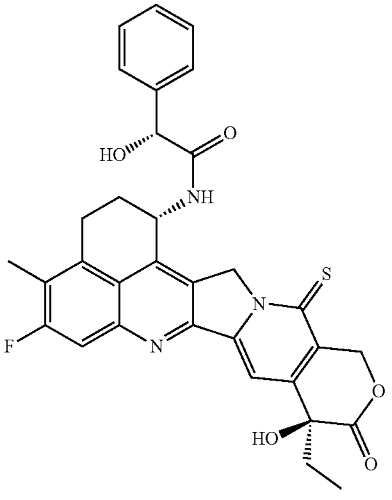
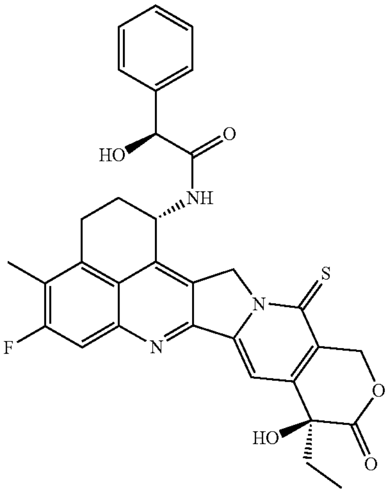
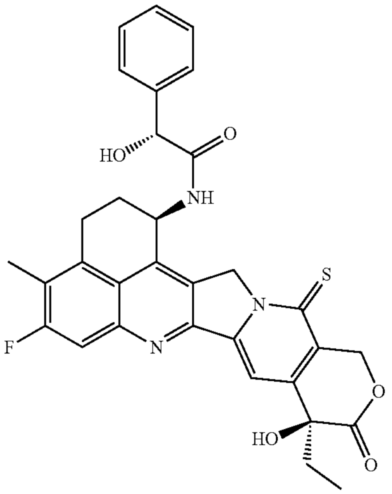

-continued
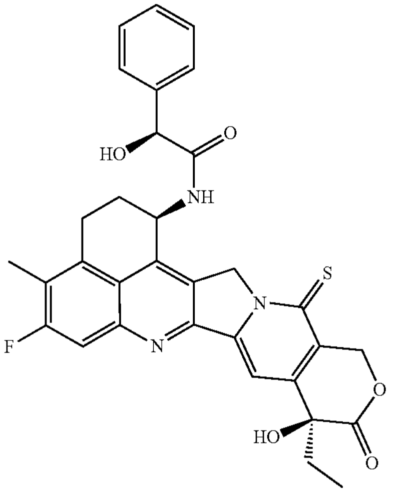
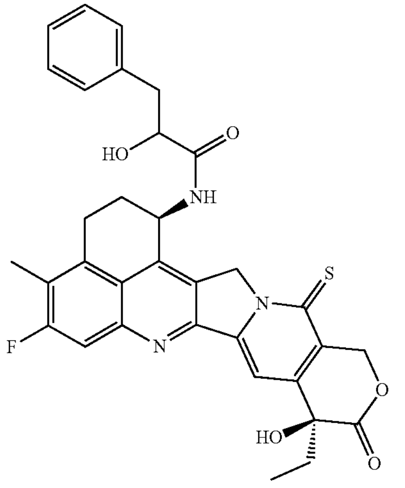
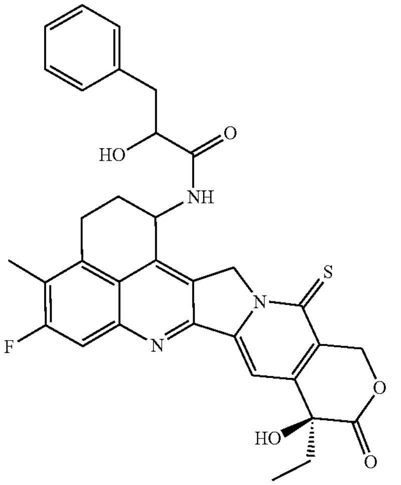
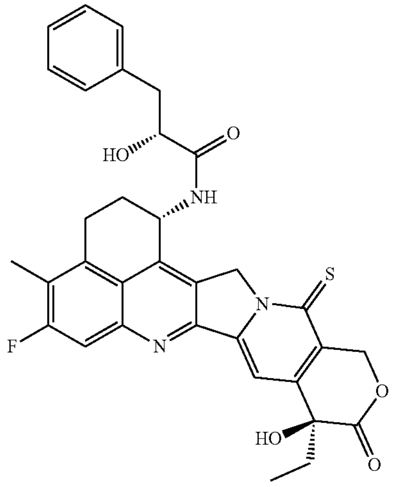
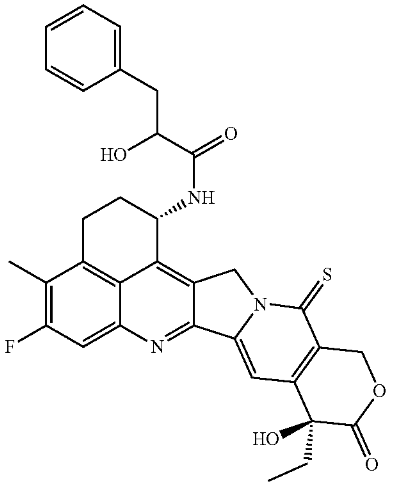
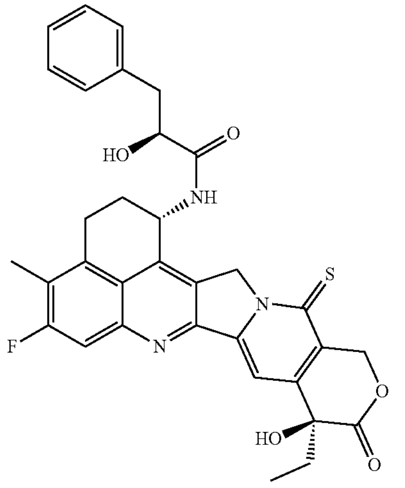
-continued -continued
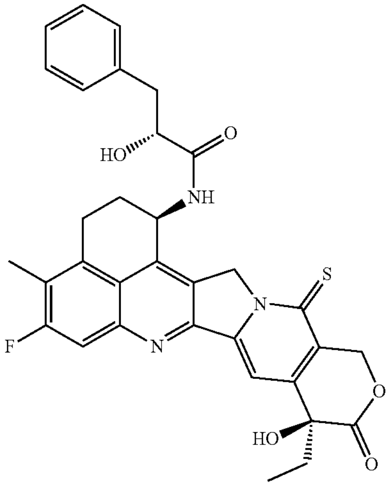
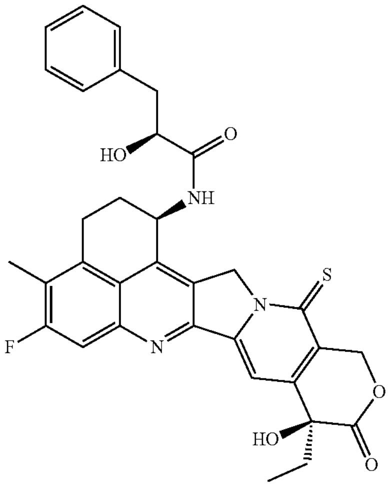
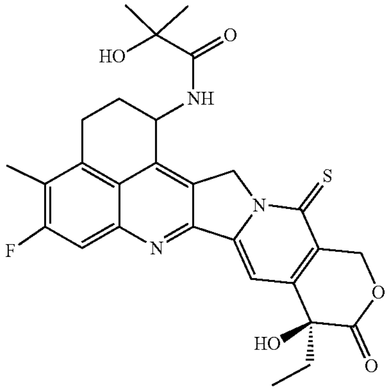
-continued
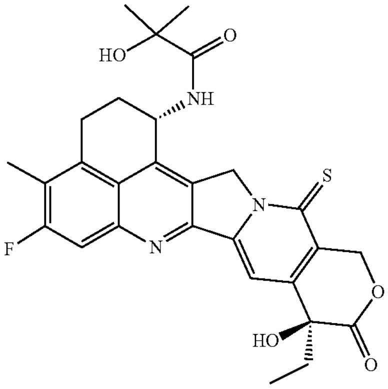
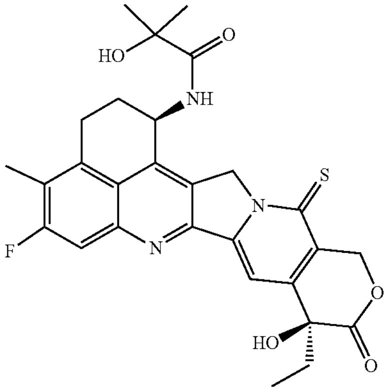
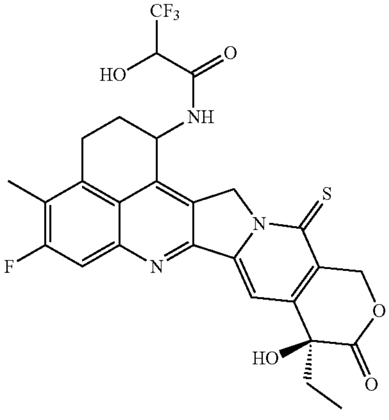
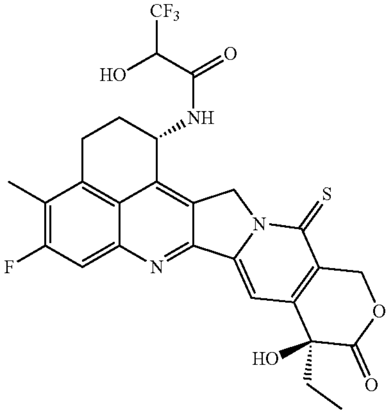

-continued
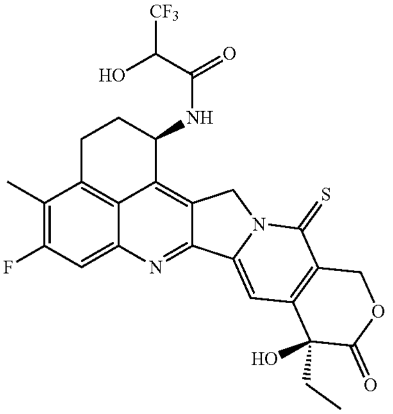
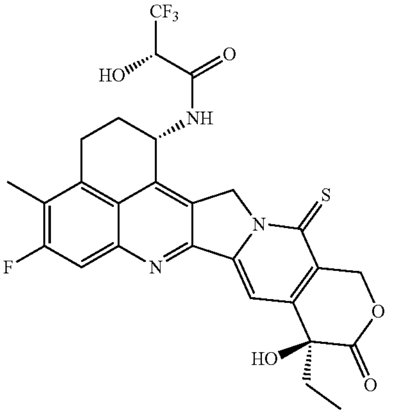
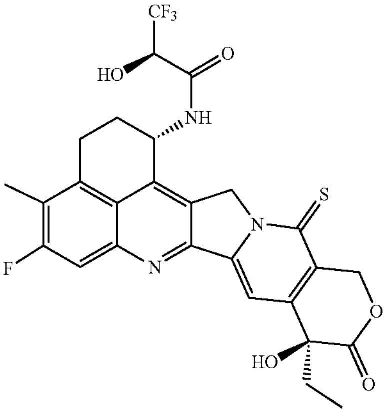
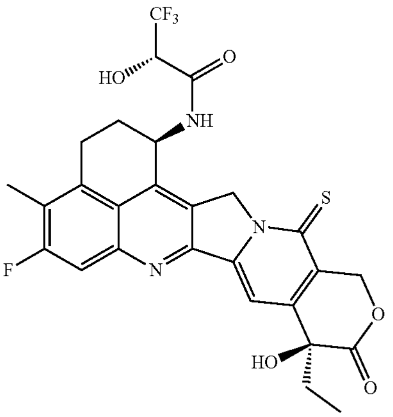
-continued
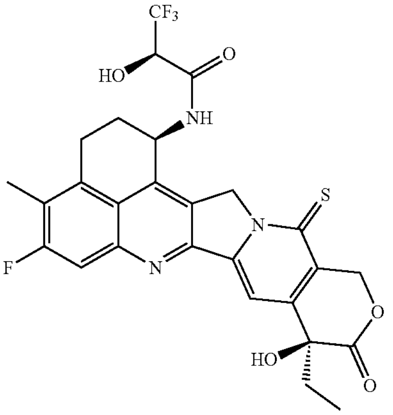
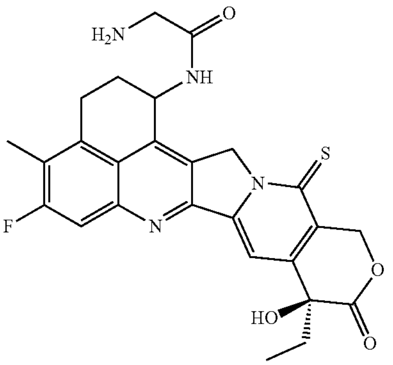
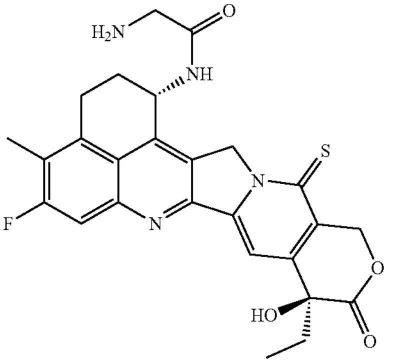
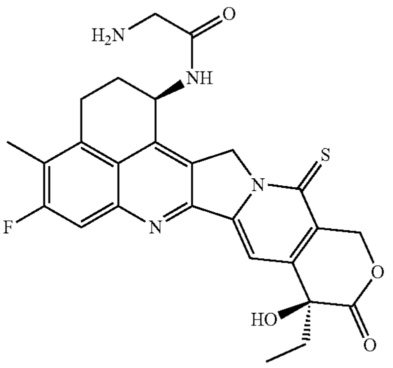

-continued
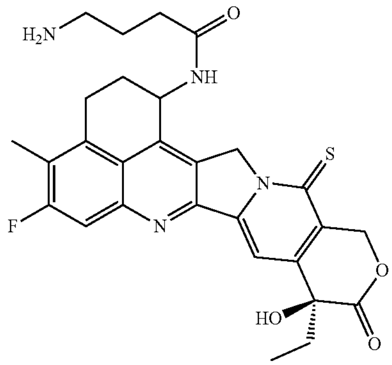
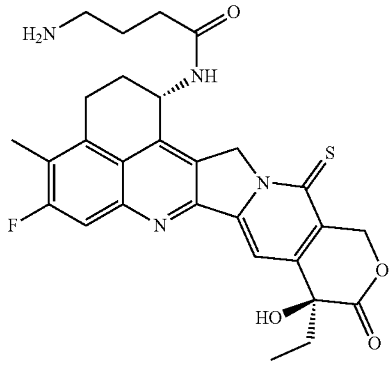
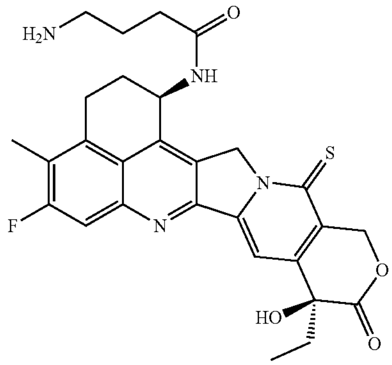
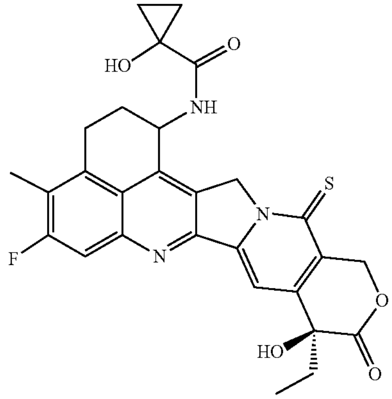
-continued
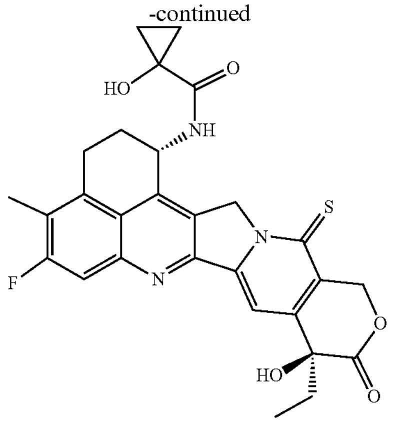
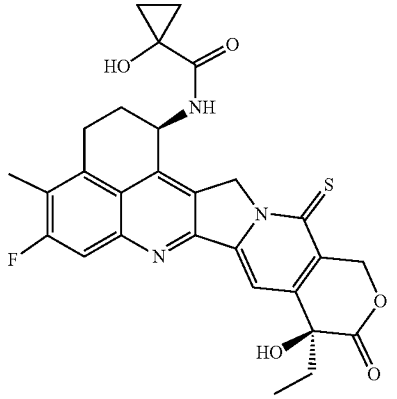
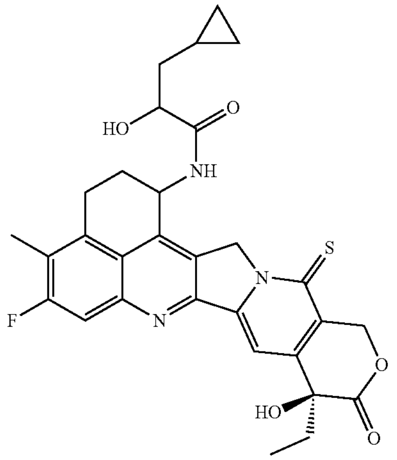
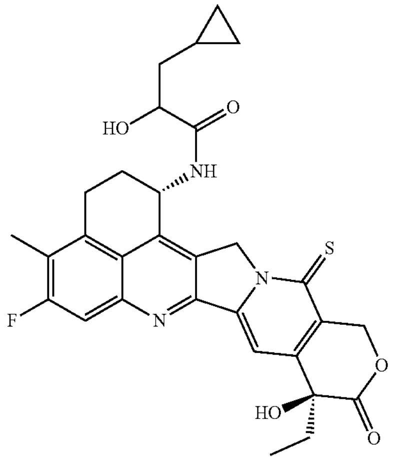

-continued
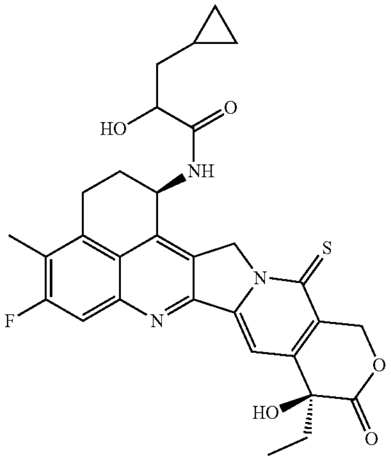
-continued
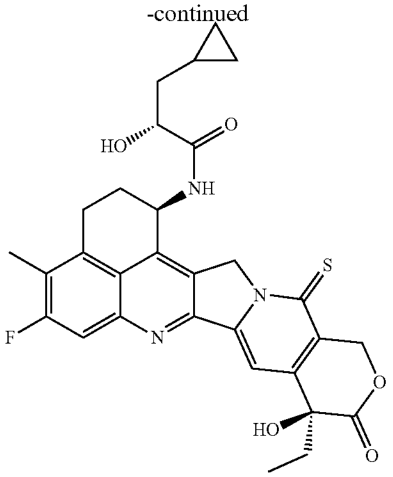
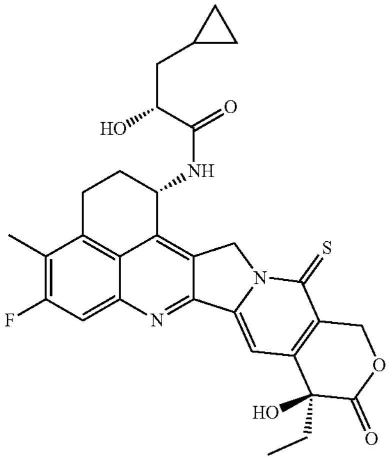
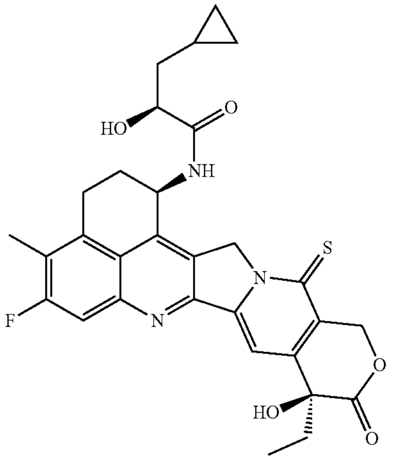
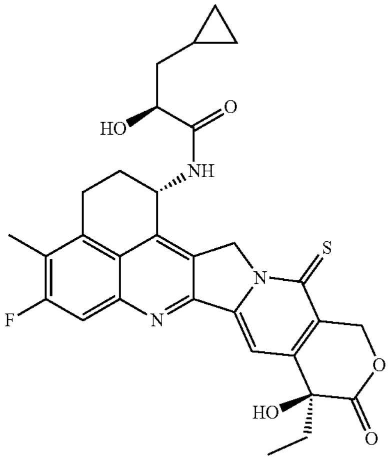
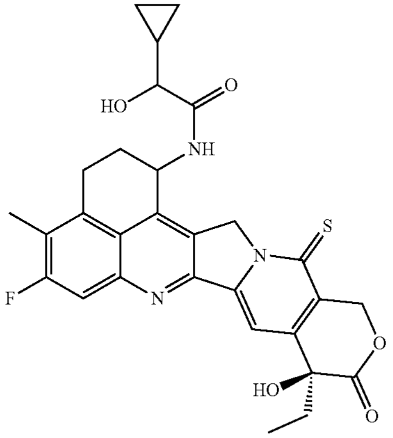

-continued
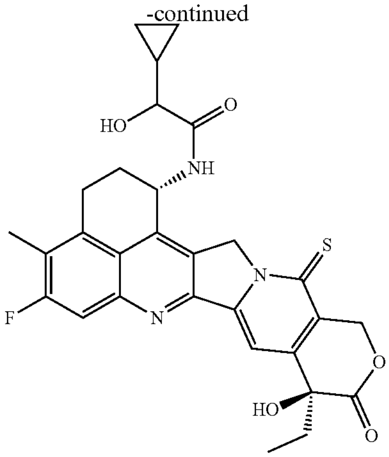
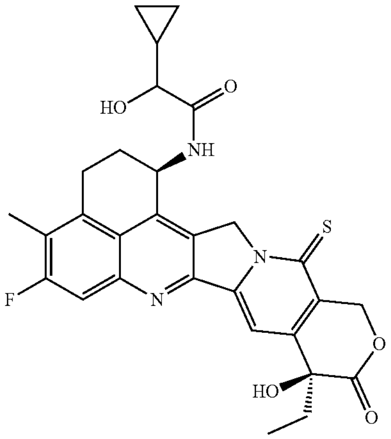
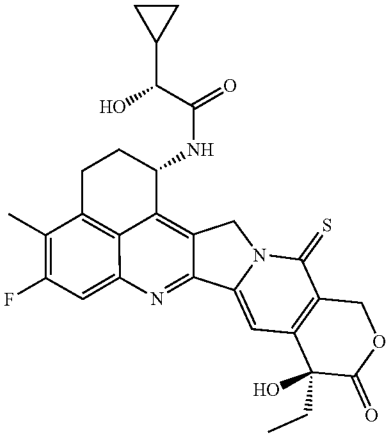
-continued
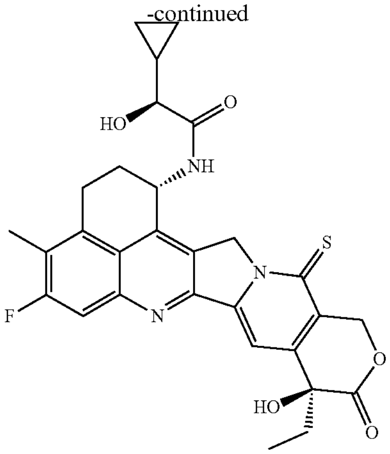
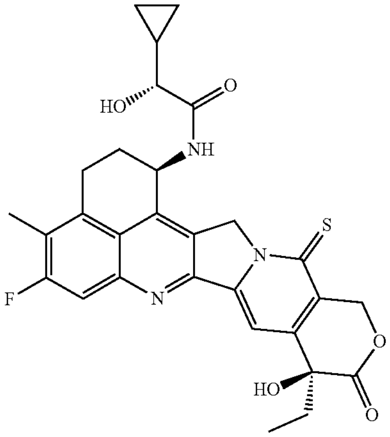
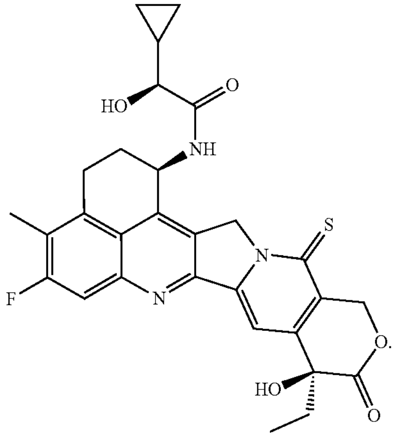
3. A pharmaceutical composition comprising a compound of formula I according to claim 1, or a pharmaceutically acceptable salt thereof, and one or more pharmaceutically acceptable excipients, diluents, or carriers.
* * * * *